US012402839B2

(12) United States Patent
Edelberg et al.

(10) Patent No.: US 12,402,839 B2
(45) Date of Patent: Sep. 2, 2025

(54) SYSTEM AND METHOD FOR DETERMINING A CARDIAC HEALTH STATUS

(71) Applicant: Prolaio, Inc., Scottsdale, AZ (US)

(72) Inventors: Jay M. Edelberg, Princeton, NJ (US); Tassos Gianakakos, Paradise Valley, AZ (US)

(73) Assignee: Prolaio, Inc., Scottsdale, AZ (US)

( * ) Notice: Subject to any disclaimer, the term of this patent is extended or adjusted under 35 U.S.C. 154(b) by 0 days.

(21) Appl. No.: 18/762,061

(22) Filed: Jul. 2, 2024

(65) Prior Publication Data
US 2024/0350095 A1    Oct. 24, 2024

Related U.S. Application Data

(63) Continuation of application No. PCT/US2023/010150, filed on Jan. 4, 2023.
(Continued)

(51) Int. Cl.
*A61B 5/361* (2021.01)
*A61B 5/00* (2006.01)
(Continued)

(52) U.S. Cl.
CPC .......... *A61B 5/7267* (2013.01); *A61B 5/0205* (2013.01); *A61B 5/256* (2021.01);
(Continued)

(58) Field of Classification Search
CPC ......... A61B 5/353; A61B 5/361; A61B 5/367; A61B 5/0205; A61B 5/318
See application file for complete search history.

(56) References Cited

U.S. PATENT DOCUMENTS

| | | | |
|---|---|---|---|
| 4,937,763 | A | 6/1990 | Mott |
| 5,009,833 | A | 4/1991 | Takeuchi et al. |

(Continued)

FOREIGN PATENT DOCUMENTS

| | | | |
|---|---|---|---|
| CN | 105512745 A | | 4/2016 |
| CN | 109871742 B | | 5/2021 |

(Continued)

OTHER PUBLICATIONS

International Search Report and Written Opinion for International PCT Application No. PCT/US23/10150 dated Jun. 16, 2023, 12 pages.
(Continued)

*Primary Examiner* — George R Evanisko
(74) *Attorney, Agent, or Firm* — HONIGMAN LLP

(57) ABSTRACT

Disclosed herein, in some aspects, are systems and methods for detecting, monitoring, and managing a cardiac health status for a subject using ECG data. In some embodiments, the system receives health parameter measurements from one or more devices that are then used by a cardiac health tool (CHT) to determine a cardiac health status. Exemplary health parameter measurements include electrocardiogram (ECG) data from an ECG device and/or weight (from a weight scale for example). As described herein, in some embodiments, determining the cardiac health status includes a) detecting a cardiac condition in the subject, b) predicting a risk of a subject developing a cardiac condition ("cardiac condition risk"), and/or c) temporal monitoring of a cardiac health status for a subject. In some embodiments, the cardiac health tool is configured to determine the efficacy of a treatment or therapy applied to reduce the severity and/or risk of a cardiac condition.

17 Claims, 26 Drawing Sheets

Related U.S. Application Data

(60) Provisional application No. 63/296,729, filed on Jan. 5, 2022, provisional application No. 63/296,734, filed on Jan. 5, 2022, provisional application No. 63/296,736, filed on Jan. 5, 2022.

(51) Int. Cl.

| | | |
|---|---|---|
| *A61B 5/0205* | (2006.01) | |
| *A61B 5/256* | (2021.01) | |
| *A61B 5/339* | (2021.01) | |
| *A61B 5/353* | (2021.01) | |
| *A61B 5/355* | (2021.01) | |
| *A61B 5/358* | (2021.01) | |
| *A61B 5/363* | (2021.01) | |
| *A61B 5/366* | (2021.01) | |
| *G16H 10/40* | (2018.01) | |
| *G16H 10/60* | (2018.01) | |
| *G16H 15/00* | (2018.01) | |
| *G16H 20/00* | (2018.01) | |
| *G16H 50/30* | (2018.01) | |
| *G16H 80/00* | (2018.01) | |

(52) U.S. Cl.
CPC .............. *A61B 5/339* (2021.01); *A61B 5/353* (2021.01); *A61B 5/355* (2021.01); *A61B 5/358* (2021.01); *A61B 5/361* (2021.01); *A61B 5/363* (2021.01); *A61B 5/366* (2021.01); *A61B 5/7275* (2013.01); *A61B 5/743* (2013.01); *A61B 5/7435* (2013.01); *G16H 10/40* (2018.01); *G16H 10/60* (2018.01); *G16H 15/00* (2018.01); *G16H 20/00* (2018.01); *G16H 50/30* (2018.01); *G16H 80/00* (2018.01)

(56) References Cited

U.S. PATENT DOCUMENTS

| | | |
|---|---|---|
| 5,063,513 A | 11/1991 | Shank et al. |
| 5,093,792 A | 3/1992 | Taki et al. |
| 5,109,700 A | 5/1992 | Hicho |
| 5,123,017 A | 6/1992 | Simpkins et al. |
| 5,173,856 A | 12/1992 | Purnell et al. |
| 5,195,046 A | 3/1993 | Gerardi et al. |
| 5,251,285 A | 10/1993 | Inoue et al. |
| 5,255,208 A | 10/1993 | Thakore et al. |
| 5,309,379 A | 5/1994 | Rawlings et al. |
| 5,390,776 A | 2/1995 | Thompson |
| 5,421,204 A | 6/1995 | Svaty, Jr. |
| 5,450,321 A | 9/1995 | Crane |
| 5,463,769 A | 10/1995 | Tate et al. |
| 5,465,321 A | 11/1995 | Smyth |
| 5,473,532 A | 12/1995 | Unno et al. |
| 5,500,940 A | 3/1996 | Skeie |
| 5,502,543 A | 3/1996 | Aboujaoude |
| 5,559,710 A | 9/1996 | Shahraray et al. |
| 5,561,431 A | 10/1996 | Peele et al. |
| 5,586,066 A | 12/1996 | White et al. |
| 5,602,733 A | 2/1997 | Rogers et al. |
| 5,612,886 A | 3/1997 | Weng |
| 5,623,109 A | 4/1997 | Uchida et al. |
| 5,663,894 A | 9/1997 | Seth et al. |
| 5,680,866 A | 10/1997 | Kangas et al. |
| 5,710,723 A | 1/1998 | Hoth et al. |
| 5,745,382 A | 4/1998 | Vilim et al. |
| 5,745,654 A | 4/1998 | Titan |
| 5,754,965 A | 5/1998 | Hagenbuch |
| 5,761,640 A | 6/1998 | Kalyanswamy et al. |
| 5,784,285 A | 7/1998 | Tamaki et al. |
| 5,808,903 A | 9/1998 | Schiltz et al. |
| 5,822,212 A | 10/1998 | Tanaka et al. |
| 5,845,230 A | 12/1998 | Lamberson |
| 5,848,396 A | 12/1998 | Gerace |
| 5,921,099 A | 7/1999 | Lee |
| 5,933,352 A | 8/1999 | Salut |
| 5,940,812 A | 8/1999 | Tengel et al. |
| 5,956,487 A | 9/1999 | Venkatraman et al. |
| 5,987,399 A | 11/1999 | Wegerich et al. |
| 5,991,525 A | 11/1999 | Shah et al. |
| 5,993,041 A | 11/1999 | Toba |
| 5,995,916 A | 11/1999 | Nixon et al. |
| 6,000,832 A | 12/1999 | Franklin et al. |
| 6,009,381 A | 12/1999 | Ono |
| 6,021,396 A | 2/2000 | Ramaswamy et al. |
| 6,026,348 A | 2/2000 | Hala |
| 6,029,149 A | 2/2000 | Dykstra et al. |
| 6,076,088 A | 6/2000 | Paik et al. |
| 6,128,540 A | 10/2000 | Van Der Vegt et al. |
| 6,131,076 A | 10/2000 | Stephan et al. |
| 6,141,647 A | 10/2000 | Meijer et al. |
| 6,141,674 A | 10/2000 | Unkrich et al. |
| 6,144,893 A | 11/2000 | Van Der Vegt et al. |
| 6,181,975 B1 | 1/2001 | Gross et al. |
| 6,202,038 B1 | 3/2001 | Wegerich et al. |
| 6,240,372 B1 | 5/2001 | Gross et al. |
| 6,277,080 B1 | 8/2001 | Nissila et al. |
| 6,356,857 B1 | 3/2002 | Qin et al. |
| 6,393,373 B1 | 5/2002 | Duyar et al. |
| 6,424,958 B1 | 7/2002 | Pappalardo et al. |
| 6,502,082 B1 | 12/2002 | Toyama et al. |
| 6,519,552 B1 | 2/2003 | Sampath et al. |
| 6,522,978 B1 | 2/2003 | Chen et al. |
| 6,556,939 B1 | 4/2003 | Wegerich |
| 6,567,752 B2 | 5/2003 | Cusumano et al. |
| 6,567,795 B2 | 5/2003 | Alouani et al. |
| 6,587,737 B2 | 7/2003 | Voser et al. |
| 6,609,036 B1 | 8/2003 | Bickford |
| 6,625,569 B2 | 9/2003 | James et al. |
| 6,651,035 B1 | 11/2003 | Lang |
| 6,775,641 B2 | 8/2004 | Wegerich et al. |
| 6,858,431 B2 | 2/2005 | Hair et al. |
| 6,859,739 B2 | 2/2005 | Wegerich et al. |
| 6,876,943 B2 | 4/2005 | Wegerich |
| 6,892,163 B1 | 5/2005 | Herzog et al. |
| 6,898,469 B2 | 5/2005 | Bickford |
| 6,917,839 B2 | 7/2005 | Bickford |
| 6,941,287 B1 | 9/2005 | Vaidyanathan et al. |
| 6,952,662 B2 | 10/2005 | Wegerich et al. |
| 6,957,172 B2 | 10/2005 | Wegerich |
| 6,975,962 B2 | 12/2005 | Wegerich et al. |
| 7,031,857 B2 | 4/2006 | Tarassenko et al. |
| 7,085,675 B2 | 8/2006 | Wegerich |
| 7,089,154 B2 | 8/2006 | Rasmussen et al. |
| 7,142,990 B2 | 11/2006 | Bouse et al. |
| 7,233,886 B2 | 6/2007 | Wegerich et al. |
| 7,308,309 B1 | 12/2007 | Koh |
| 7,308,385 B2 | 12/2007 | Wegerich et al. |
| 7,318,808 B2 | 1/2008 | Tarassenko et al. |
| 7,373,283 B2 | 5/2008 | Herzog et al. |
| 7,403,869 B2 | 7/2008 | Wegerich et al. |
| 7,409,320 B2 | 8/2008 | Wegerich |
| 7,539,597 B2 | 5/2009 | Wegerich et al. |
| 7,640,145 B2 | 12/2009 | Wegerich et al. |
| 7,647,185 B2 | 1/2010 | Tarassenko et al. |
| 7,670,295 B2 | 3/2010 | Sackner et al. |
| 7,739,096 B2 | 6/2010 | Wegerich et al. |
| 7,818,131 B2 | 10/2010 | Mott |
| 7,941,209 B2 | 5/2011 | Hughes et al. |
| 7,941,701 B2 | 5/2011 | Wegerich et al. |
| 8,239,170 B2 | 8/2012 | Wegerich |
| 8,290,575 B2 | 10/2012 | Tarassenko et al. |
| 8,332,017 B2 | 12/2012 | Tarassenko et al. |
| 8,478,542 B2 | 7/2013 | Mott |
| 8,515,680 B2 | 8/2013 | Pipke et al. |
| 8,597,185 B2 | 12/2013 | Pipke |
| 8,620,591 B2 | 12/2013 | Wegerich |
| 9,427,377 B1 | 8/2016 | Miceli et al. |
| 9,693,727 B1 | 7/2017 | Saalasti et al. |
| 10,586,619 B1 | 3/2020 | Richards |
| 11,488,702 B2 | 11/2022 | Richards |
| 2003/0055666 A1 | 3/2003 | Roddy et al. |
| 2003/0126258 A1 | 7/2003 | Conkright et al. |
| 2005/0228591 A1 | 10/2005 | Hur et al. |

(56) References Cited

U.S. PATENT DOCUMENTS

| | | | |
|---|---|---|---|
| 2005/0236004 | A1 | 10/2005 | Magnuson et al. |
| 2005/0261837 | A1 | 11/2005 | Wegerich et al. |
| 2006/0293859 | A1 | 12/2006 | Pipke et al. |
| 2007/0149862 | A1 | 6/2007 | Pipke |
| 2008/0071501 | A1 | 3/2008 | Herzog |
| 2008/0312513 | A1 | 12/2008 | Simon et al. |
| 2009/0177443 | A1 | 7/2009 | Nikovski et al. |
| 2011/0029250 | A1 | 2/2011 | Mott |
| 2011/0087115 | A1 | 4/2011 | Sackner et al. |
| 2011/0093244 | A1 | 4/2011 | Pipke et al. |
| 2011/0124982 | A1 | 5/2011 | Pipke |
| 2011/0137297 | A1 | 6/2011 | Kiani et al. |
| 2011/0172504 | A1 | 7/2011 | Wegerich |
| 2011/0224565 | A1 | 9/2011 | Ong et al. |
| 2011/0257555 | A1 | 10/2011 | Banet et al. |
| 2012/0029320 | A1 | 2/2012 | Watson et al. |
| 2013/0060156 | A1 | 3/2013 | Gregg et al. |
| 2013/0079646 | A1 | 3/2013 | Bhunia et al. |
| 2013/0144146 | A1 | 6/2013 | Linker |
| 2014/0107433 | A1 | 4/2014 | Wegerich |
| 2014/0194763 | A1 | 7/2014 | Narayan |
| 2014/0304204 | A1 | 10/2014 | Cameron et al. |
| 2016/0256064 | A1 | 9/2016 | Estes, Jr. |
| 2018/0113986 | A1 | 4/2018 | Zhu |
| 2018/0177415 | A1 | 6/2018 | Madl |
| 2018/0325460 | A1 | 11/2018 | Wegerich |
| 2019/0132948 | A1 | 5/2019 | Longinotti-Buitoni et al. |
| 2019/0175026 | A1 | 6/2019 | Verzal et al. |
| 2019/0236447 | A1 | 8/2019 | Cohen et al. |
| 2020/0260979 | A1 | 8/2020 | Cao et al. |
| 2020/0273567 | A1 | 8/2020 | Petterson et al. |
| 2021/0000449 | A1 | 1/2021 | Deo et al. |
| 2021/0020293 | A1 | 1/2021 | Richards |
| 2021/0330224 | A1 | 10/2021 | Al-Ali et al. |
| 2021/0338174 | A1 | 11/2021 | Weffers-Albu et al. |
| 2021/0350931 | A1 | 11/2021 | Dawoud et al. |
| 2022/0192596 | A1 | 6/2022 | Fathieh et al. |
| 2023/0033967 | A1 | 2/2023 | Richards |
| 2023/0076069 | A1* | 3/2023 | Lange ................ A61B 5/349 |
| 2024/0032853 | A1 | 2/2024 | Sekaric et al. |

FOREIGN PATENT DOCUMENTS

| | | | |
|---|---|---|---|
| WO | 2007147166 | A3 | 12/2008 |
| WO | 2019161277 | A1 | 8/2019 |
| WO | 2020257609 | A1 | 12/2020 |
| WO | 2021011381 | A1 | 1/2021 |
| WO | 2022047004 | A1 | 3/2022 |
| WO | 2023133163 | A1 | 7/2023 |
| WO | 2023133165 | A1 | 7/2023 |
| WO | 2024025932 | A1 | 2/2024 |

OTHER PUBLICATIONS

International Search Report and Written Opinion for International PCT Application No. PCT/US23/10147 dated Apr. 26, 2023, 10 pages.

International Search Report and Written Opinion for International PCT Application No. PCT/US2023/010149 dated Mar. 31, 2023, 16 pages.

Abut et al., Machine learning and statistical methods for the prediction of maximal oxygen uptake: recent advances. Medical Devices: Evidence and Research, 8, 369-379, 2015.

Akay, M.F. et al., "Support vector regression and multilayer feed forward neural networks for non-exercise prediction of VO2max", ISSN 0957-4174, Expert Systems With Applications, Aug. 1, 2009, Elsevier, Amsterdam, NL, vol. 36, Nr.: 6, pp. 10112-10119.

Altini, M.et al., Cardiorespiratory fitness estimation in free-living using wearable sensors. Artificial Intelligence in Medicine, 68, 32 pages, 2016.

Altini, M. et al., Personalization of energy expenditure and cardiorespiratory fitness estimation using wearable sensors in supervised and unsupervised free-living conditions. Eindhoven University of Technology. 243 pages, 2015.

Altini, M. et al., Personalized cardiorespiratory fitness and energy expenditure estimation using hierarchical Bayesian models. Journal of Biomedical Informatics, 56, pp. 195-204, 2015.

Altini, M. et al., Relation Between Estimated Cardiorespiratory Fitness and Running Performance in Free-Living: an analysis of HRV4Training data, ResearchGate, 5 pages, 2017.

Altini, M. et al., Automatic Heart Rate Normalization for Accurate Energy Expenditure Estimation, Methods of Information in Medicine, 53(5), 7 pages, 2014.

Baig, Physiological Control of Human Heart Rate and Oxygen Consumption during Rhythmic Exercises. 137 pages, 2014.

Bang et al. "A pulse transit time measurement method based on electrocardiogramand bioimpedance," 2009 IEEE Biomedical Circuits and Systems Conference 153-156.

Baralis et al., "Predicting Cardiopulmonary Response to Incremental Exercise Test,"; 2015 IEEE 28th International Symposium on Computer-Based Medical Systems, 2015, pp. 135-140, 2015.

Bauer et al. Use of the scored Patient-Generated Subjective Global Assessment (PG-SGA) as a nutrition assessment tool in patients with cancer, European Journal of Clinical Nutrition,56, pp. 779-785, 2002.

Burke et al. "An improved micro-power pre-amplifier for dry-electrode ECG recording," Proc. 11th WSEAS Int. Conf. Circuits. 2007:234-239.

Cao, Z. et al., Predicting Vo2max with an Objectively Measured Physical Activity in Japanese Women. Medicine and Science in Sports and Exercise, 179-186, 2009.

Cheng, et al., "Training and Evaluation of Human Cardiorespiratory Endurance Based on a Fuzzy Algorithm."; International Journal of Environmental Research and Public Health, 16, 2390, 20 pages, 2019.

Choi et al. Process monitoring using a Gaussian mixture model via principal component analysis and discriminant analysis, Computers and Chemical Engineering, 28, pp. 1377-1387, 2004.

De Brabandere, B. et al., Dynamic Filter Networks, 9 pages, 2016.

Edwards, H. et al., Towards a Neural Statistician, ICLR, 1-13, 2017.

Eslami et al., Neural scene representation and rendering, Science, vol. 360, No. 6394, pp. 1204-1210, 2018.

Firstbeat Technologies Ltd., Automated Fitness Level (VO2max) Estimation with Heart Rate and Speed Data, 1-9, 2014.

Garnelo, M. et al., Neural Processes. 11 pages, 2018.

Garnelo, M. et al., Conditional Neural Processes, 10 pages, 2018.

Gong, J. et al., Convolutional Interaction Network for Natural Language Inference. Proceedings of the 2018 Conference on Empirical Methods in Natural Language Processing (EMNLP 2018), pp. 1576-1585, 2018.

Ha et al., HyperNetworks, 29 pages, 2016.

Hewitt, L. B. et al., The Variational Homoencoder: Learning to learn high capacity generative models from few examples. 10 pages, 2018.

Hunt, K. J., et al., Identification of heart rate dynamics during moderate-to-vigorous treadmill exercise. BioMedical Engineering Online, 14(1), pp. 1-13, 2015.

Int'l Preliminary Report on Patentability and Written Opinion issued in Int'l Patent No. PCT/US2006/045656 mailed Aug. 8, 2007.

Int'l Search Report and Written Opinion issued in Int'l Application No. PCT/US11/20094 issued on Mar. 22, 2011.

Int'l Search Report and Written Opinion issued in Int'l Patent Applicaiton No. PCT/US2023/077462 dated Dec. 1, 2024, 12 pages.

Int'l Search Report and Written Opinion issued in Int'l Patent Applicaiton No. PCTUS2023/028665 dated Nov. 15, 2023, 6 pages.

Int'l Search Report and Written Opinion issued in Int'l Patent Application No. PCT/US2020/041611, dated Aug. 5, 2020, 7 pages.

Jia, N. et al., An Exercise Health Simulation Method Based on Integrated Human Thermophysiological Model. 15 pages, 2017.

Kaiser, L. et al., Depthwise Separable Convolutions for Neural Machine Translation, 1-10, 2017.

(56) References Cited

OTHER PUBLICATIONS

Kim, Z. et al., Modeling long-term human activeness using recurrent neural networks for biometric data. BMC Medical Informatics and Decision Making, 17(S1), 57. 15 pages, 2017.

Lee et al., Deep Neural Networks as Gaussian Processes, ICLR, 1-17, 2018.

Malek, M. et al., A New Non-Exercise-Based VO2Max Prediction Equation for Aerobically Trained Men, Journal of Strength and Conditioning Research, 19(3), 559-565, 2005.

Nairac et al., Choosing an appropriate model for novelty detection, Artificial Neural Networks, Publ. No. 440, vol. No., pp. 117-122, Jul. 7-9, 1997.

Nes, B. M. et al., Estimating VO2 speak from a nonexercise prediction model: The Hunt Study, Norway. Medicine and Science in Sports and Exercise, 43(11), 1-20, 2011.

Patterson et al. "A flexible, low noise reflective PPG sensor platform for ear-worn heart rate monitoring." 2009 sixth international workshop on wearable and implantable body sensor networks. IEEE, 2009:286-291.

Peters, M. et al., Deep contextualized word representations, Proceedings of NAACL-HLT, pp. 2227-2237, 2018.

Plasqui et al., Accelerometry and Heart Rate as a Measure of Physical Fitness: Cross-Validation. Medicine and Science in Sports and Exercise, 38(8), 1510-1514, 2006.

Povinelli et al., Time Series classification using Gaussian mixture models of reconstructed phase spaces, IEE Transactions on Knowledge and Data Engineering, vol. 16(6); pp. 779-783, Jun. 2004.

Ruder, S., An Overview of Multi-Task Learning in Deep Neural Networks, 1-14, 2017.

Seoane et al. "An analog front-end enables electrical impedance spectroscopy system on-chip for biomedical applications," Physiological measurement 29.6 (2008): S267-S278.

Shen et al., Learning Context-Sensitive Convolutional Filters for Text Processing, 10 pages, 2018.

Silva, G. et al., Calculation and validation of models for estimating VO 2max from the 20-m shuttle run test in children and adolescents, Archives of Exercise in Health and Disease, 145-152, 2012.

Su, S. et al., Dynamic Modelling of Heart Rate Response Under Different Exercise Intensity, The Open Medical Informatics Journal, 4, 81-85, 2010.

Su, S. et al., Modelling and Control for Heart Rate Regulation during Treadmill Exercise, 2006 International Conference of the IEEE Engineering in Medicine and Biology Society , 1, 4299-4302, 2006.

Swain, D. et al., Validation of a New Method for Estimating VO2max Based on VO2 Reserve, Medicine and Science in Sports and Exercise, (14), 1421-1426, 2004.

Tarassenko et al., Integrated monitoring and analysis for early warning of patient deterioration, British Journal of Anaesthesia, 97(1):64-8, 2006.

Tarassenko et al., Biosigntm: multi-parameter monitoring for early warning of patient deterioration, Medical Applications of Signal Processing, The 3rd IEE International Seminar on (Ref. No. 2005-1119), vol. No., pp. 71,76,Nov. 3-4, 2005.

Teng et al. "Wearable medical systems for p-health," IEEE reviews in Biomedical engineering 1 (2008):62-74.

Tonis, T. et al., Comparing VO2max determined by using the relation between heart rate and accelerometry with submaximal estimated VO2max, Journal of Sports Medicine and Physical Fitness, 52(4), 337-343, 2012.

Van den Oord, A. et al., Conditional Image Generation with PixelCNN Decoders, 1-13, 2016.

Wong, Analysis and augmentation of a multi-parameter monitoring system for early warning of patient deterioration, pp. 19-21, Dec. 2007.

Wu, F. et al., Pay Less Attention With Lightweight and Dynamic Convolutions, 1-14, 2019.

* cited by examiner

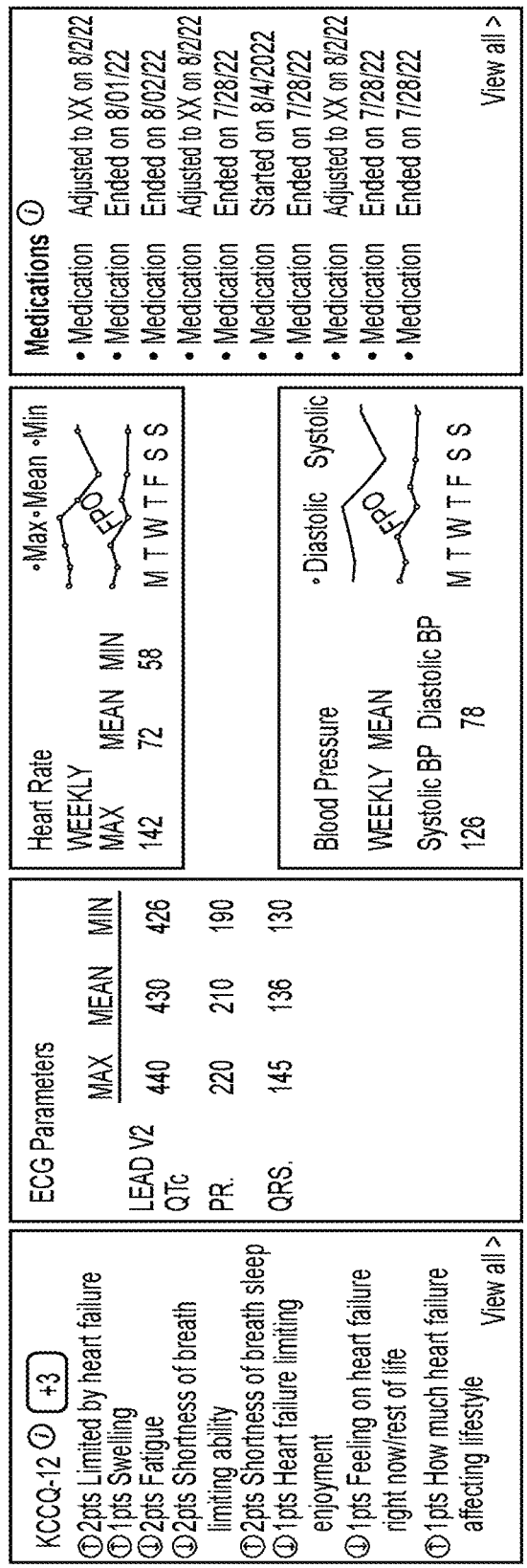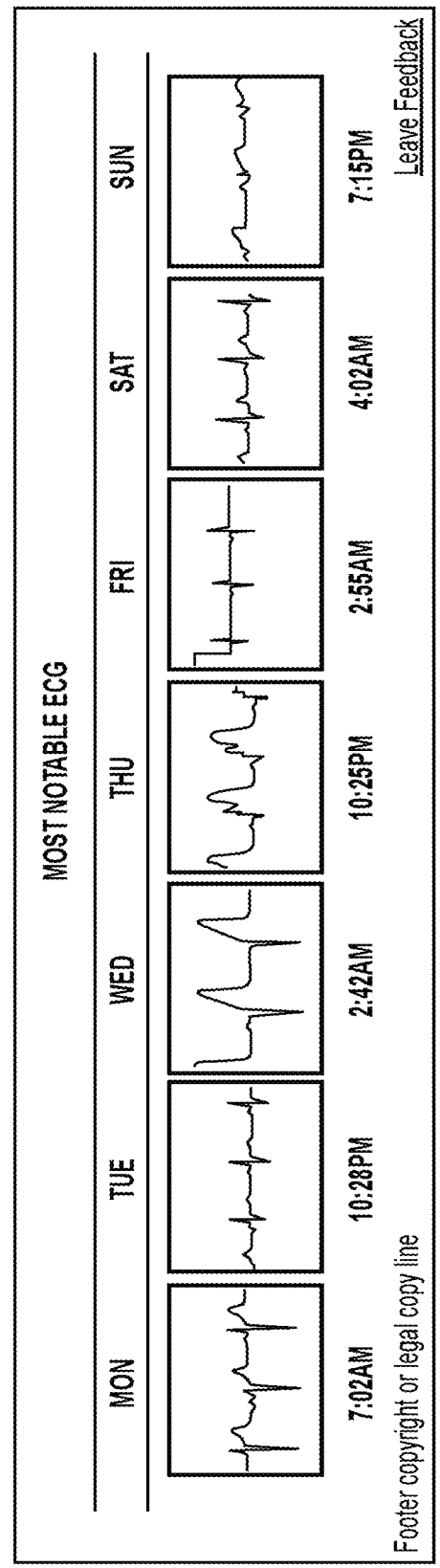
FIG. 15 (Cont.)

☐ Increase in Risk
○ Reduction in Risk
△ No Change in Risk

👤 Jay Edelberg

| Monitoring status | | | | Action ▽ Date ↕ | Status ▽ | 🔖 |
|---|---|---|---|---|---|---|
| ECG | KCCQ-12 | BP | Weight | | | |
| ▽ | ▽ | ▽ | ▽ | | | |
| ○ | ○ | ○ | ○ | 🗑 Engage patient today 11/15/22 - JE | ☑ 11/17/22 - GH | 🔖 ⌄ |
| ○ | ○ | ○ | △ | 🗑 Bring in patient <5d 11/15/22 - JE | ☑ 11/17/22 - GH | 🔖 ⌄ |
| △ | ○ | ○ | ○ | 🗑 Check devices/ compliance 11/15/22 - JE | ☐ | 🔖 ⌄ |
| ○ | ○ | ○ | ○ | 🗑 Check devices/ compliance 11/15/22 - GH | ☐ | 🔖 ⌄ |
| ○ | ○ | ○ | ○ | 🗑 Continue as-is 11/15/22 - JE | ☐ | 🔖 ⌄ |
| ○ | ○ | ○ | ○ | | | 🔖 ⌄ |
| ○ | ☐ | ○ | ○ | 🗑 Nurse call patient 11/15/22 - JE | ☐ | 🔖 ⌄ |
| ○ | ○ | ○ | ○ | 🗑 Other 11/15/22 - JE | ☑ 11/17/22 - GH | 🔖 ⌄ |
| ○ | ○ | ○ | ○ | 🗑 Continue as-is 11/15/22 - JE | ☐ | 🔖 ⌄ |
| ○ | ○ | ○ | ○ | 🗑 Continue as-is 11/15/22 - JE | ☐ | 🔖 ⌄ |
| ○ | ○ | ○ | ○ | 🗑 Continue as-is 11/15/22 - JE | ☐ | 🔖 ⌄ |

< Metrics

PROLAIO

ALL PATIENTS

PATIENT SUMMARY

| | Patient Name<br>Study # (if have one)<br>Age, Gender<br>Last Admission Date | 58 y/o woman 2 weeks post discharge from 5d HF admission associated with atrial fibrillation and myocardial ischemia. Atrial fibrillation since discharge. Key risk parameters increased over past week. The Prolaio nurse contacted this patient 2 times since discharge. |
|---|---|---|
| | Patient Name<br>Study # (if have one)<br>Age, Gender<br>Last Admission Date | 58 y/o woman 1 week post discharge from 5d HF admission associated with atrial fibrillation and myocardial ischemia. Key risk parameters increased since past week. |
| | Patient Name<br>Study # (if have one)<br>Age, Gender<br>Last Admission Date | 58 y/o woman 2 weeks post discharge from 5d HF admission associated with atrial fibrillation and myocardial ischemia. Key risk parameters increased since past week. |
| | Patient Name<br>Study # (if have one)<br>Age, Gender<br>Last Admission Date | 58 y/o male 3 weeks post discharge from 5d HF admission associated with atrial fibrillation and myocardial ischemia. Key risk parameters reduced since past week. |
| | Patient Name<br>Study # (if have one)<br>Age, Gender<br>Last Admission Date | 58 y/o male 2 weeks post discharge from 5d HF admission associated with atrial fibrillation and myocardial ischemia. Key risk parameters reduced since past week. |

User Name 👤 Last login: 7/5/2022 08:10:00

🔍 Search

KEY RISKS ▽   CARDIOVASCULAR MEDS ▽   VIEWED TODAY ▽

⚠ Increased Sleeping Heart Rate
Increased Respiratory Rate
Increased ST Segment

Medication, Change 07/05/22
Medication, Change 07/04/22 ✓

❗ Increased Sleeping Heart Rate
Increased Sleeping Respiratory Rate
Increased ST Segment Medication, Change 05/02/22
Medication, Change 05/25/22 ✓

❗ Increased Sleeping Respiratory Rate
Increased AF burden
Increased ST Segment

Medication, Change 07/01/22

✓ Reduced Sleeping Heart Rate
Reduced ST Segment

Medication, Change 01/02/22

✓ Reduced Sleeping Heart Rate
Reduced Sleeping Respiratory Rate

Medication, Change 05/14/22

FIG. 18 (Cont. 2)

SYSTEM AND METHOD FOR DETERMINING A CARDIAC HEALTH STATUS

CROSS-REFERENCE TO RELATED APPLICATIONS

This application is a continuation of International Patent Application No. PCT/US2023/010150, filed on Jan. 4, 2023, which claims the benefit of and priority to U.S. Provisional Patent Application No. 63/296,729, filed Jan. 5, 2022, U.S. Provisional Patent Application No. 63/296,734, filed on Jan. 5, 2022, and U.S. Provisional Patent Application No. 63/296,736, filed on Jan. 5, 2022, the entire contents of each of which are incorporated by reference herein.

BACKGROUND

Current monitoring of cardiovascular health outside of a hospital or other medical facility can involve ECG analysis, and other inputs that include heart rate, blood pressure and weight. Such data, taken as a whole can provide healthcare providers some insight into the condition of a patient. However, in many scenarios, particularly patients either having a cardiac condition or those at risk of developing a cardiac condition, healthcare providers require such patients to come into a hospital or other medical facility to perform a more complete analysis of the cardiovascular health of the patient. Therefore, there is a need for a more robust monitoring of cardiovascular health in an outpatient setting.

SUMMARY

Disclosed herein in some aspects is a non-transitory computer readable medium for determining a cardiac health status for a subject, the non-transitory computer readable medium comprising instructions that, when executed by a processor, cause the processor to perform operations including: a) obtaining electrocardiogram (ECG) data captured from the subject via an ECG device; b) extracting one or more parameters associated with the ECG data; c) detecting left atrial enlargement (LAE) within the subject by applying a first decision engine with the extracted one or more parameters from the ECG data; and d) determining the cardiac health status by applying a second decision engine based on the left atrial enlargement detection; wherein the cardiac health status comprises i) a detected first cardiac condition, ii) a calculated risk score for developing the first cardiac condition by the subject, iii) a change from a previous cardiac health status, or iv) any combination thereof.

In some embodiments, the operations further include applying a third decision engine to adjust the cardiac health status based on i) detection of a second cardiac condition or ii) calculation of a risk score for developing the second cardiac condition by the subject. In some embodiments, one or both of the first cardiac condition and the second cardiac condition comprise a cardiac disease. In some embodiments, the first cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof. In some embodiments, the second cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof. In some embodiments, the first cardiac condition comprises an atrial fibrillation risk score. In some embodiments, the second cardiac condition comprises cardiomyopathy and/or diastolic dysfunction.

In some embodiments, one or both of the first decision engine and the second decision engine comprises a trained model, a decision tree, an analytical expression, or a combination thereof. In some embodiments, the first decision engine applies one or more clinical biomarker data, one or more imaging data, one or more clinical data, or a combination thereof, to detect LAE in the subject. In some embodiments, the second decision engine applies one or more clinical biomarker data, one or more imaging data, one or more clinical data, the one or more extracted ECG parameters, or a combination thereof, to determine the cardiac health status. In some embodiments, the third decision engine applies one or more clinical biomarker data, one or more imaging data, one or more clinical parameters, the one or more extracted ECG parameters, or a combination thereof, to adjust the cardiac health status.

In some embodiments, the clinical biomarker data comprises data for one or more of B-type natriuretic peptide (BNP), N-terminal (NT)-pro hormone BNP (NT-proBNP), and cardiac troponin. In some embodiments, the one or more imaging data comprises one or both of an echocardiogram image and a cardiac MRI. In some embodiments, the one or more clinical parameters comprises, the subject's age, sex, weight, body mass index, height, physiological data, exercise testing results, heart rate, activity levels, velocity, sleep data, or a combination thereof. In some embodiments, the ECG device comprises a 12-lead device, a 6-lead device, a 1-lead device, or a 2-lead device. In some embodiments, the ECG device comprises a wearable device.

Disclosed herein, in some aspects, is a method for determining a cardiac health status for a subject, the method comprising: a) obtaining electrocardiogram (ECG) data captured from the subject via an ECG device; b) extracting one or more parameters associated with the ECG data; c) detecting left atrial enlargement (LAE) within the subject by applying a first decision engine with the extracted parameters from the ECG data; and determining the cardiac health status by applying a second decision engine with the left atrial enlargement detection; wherein the cardiac health status comprises i) a detected first cardiac condition, ii) a calculated risk score for developing the first cardiac condition by the subject, iii) a change from a previous cardiac health status, or iv) any combination thereof.

In some embodiments, the method further comprises applying a third decision engine to adjust the cardiac health status based on i) detection of a second cardiac condition or ii) calculation of a risk score for developing the second cardiac condition by the subject.

In some embodiments, one or both of the first cardiac condition and the second cardiac condition comprise a cardiac disease. In some embodiments, the first cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof. In some embodiments, the second cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof. In some embodiments, the first cardiac condition comprises an atrial fibrillation risk score. In some embodiments, the second cardiac condition comprises cardiomyopathy and/or diastolic dysfunction.

In some embodiments, one or both of the first decision engine and the second decision engine comprises a trained model, a decision tree, an analytical expression, or a combination thereof. In some embodiments, detecting LAE in the subject comprises the first decision engine applying one or more clinical biomarker data, one or more imaging data, one or more clinical data, or a combination thereof. In some embodiments, determining the cardiac health status comprises the second decision engine applying one or more clinical biomarker data, one or more imaging data, one or more clinical data, the one or more extracted ECG parameters, or a combination thereof. In some embodiments, the third decision engine applies one or more clinical biomarker data, one or more imaging data, one or more clinical parameters, the one or more extracted ECG parameters, or a combination thereof, to adjust the cardiac health status.

In some embodiments, the clinical biomarker data comprise data for one or more of B-type natriuretic peptide (BNP), N-terminal (NT)-pro hormone BNP (NT-proBNP), and cardiac troponin. In some embodiments, the one or more imaging data comprises one or both of an echocardiogram image and a cardiac MRI. In some embodiments, the one or more clinical parameters comprises, the subject's age, sex, weight, body mass index, height, physiological data, exercise testing results, heart rate, activity levels, velocity, sleep data, or a combination thereof. In some embodiments, the ECG device comprises a 12-lead device, a 6-lead device, a 1-lead device, or a 2-lead device. In some embodiments, the ECG device comprises a wearable device.

Disclosed herein, in some aspects, is a system for determining a cardiac health status for a subject, the system comprising: a) one or more processors; and b) one or more memories storing instructions that, when executed by the one or more processors, cause the system to perform operations including: 1) obtaining electrocardiogram (ECG) data captured from the subject via an ECG device; 2) extracting one or more parameters associated with the ECG data; 3) detecting left atrial enlargement (LAE) within the subject by applying a first decision engine with the extracted one or more parameters from the ECG data; and 4) determining the cardiac health status by applying a second decision engine based on the left atrial enlargement detection; wherein the cardiac health status comprises i) a detected first cardiac condition, ii) a calculated risk score for developing the first cardiac condition by the subject, iii) a change from a previous cardiac health status, or iv) any combination thereof.

In some embodiments, the operations further include applying a third decision engine to adjust the cardiac health status based on i) detection of a second cardiac condition or ii) calculation of a risk score for developing the second cardiac condition by the subject.

In some embodiments, one or both of the first cardiac condition and the second cardiac condition comprise a cardiac disease. In some embodiments, the first cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof. In some embodiments, the second cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof. In some embodiments, the first cardiac condition comprises an atrial fibrillation risk score. In some embodiments, the second cardiac condition comprises cardiomyopathy and/or diastolic dysfunction.

In some embodiments, one or both of the first decision engine and the second decision engine comprises a trained model, a decision tree, an analytical expression, or a combination thereof. In some embodiments, the first decision engine applies one or more clinical biomarker data, one or more imaging data, one or more clinical data, or a combination thereof, to detect LAE in the subject. In some embodiments, the second decision engine applies one or more clinical biomarker data, one or more imaging data, one or more clinical data, the one or more extracted ECG parameters, or a combination thereof, to determine the cardiac health status. In some embodiments, the third decision engine applies one or more clinical biomarker data, one or more imaging data, one or more clinical parameters, the one or more extracted ECG parameters, or a combination thereof, to adjust the cardiac health status.

In some embodiments, the clinical biomarker data comprises data for one or more of B-type natriuretic peptide (BNP), N-terminal (NT)-pro hormone BNP (NT-proBNP), and cardiac troponin. In some embodiments, the one or more imaging data comprises one or both of an echocardiogram image and a cardiac MRI. In some embodiments, the one or more clinical parameters comprises, the subject's age, sex, weight, body mass index, height, physiological data, exercise testing results, heart rate, activity levels, velocity, sleep data, or a combination thereof. In some embodiments, the ECG device comprises a 12-lead device, a 6-lead device, a 1-lead device, or a 2-lead device. In some embodiments, the ECG device comprises a wearable device.

Disclosed herein, in some aspects, is a non-transitory computer readable medium for determining a cardiac health status in a subject, the non-transitory computer readable medium comprising instructions that, when executed by a processor, cause the processor to perform operations including: a) obtaining electrocardiogram (ECG) data captured from the subject via an ECG device; b) extracting one or more P wave parameters associated with the ECG data; c) identifying one or more changes in the extracted P wave parameters from previous ECG data of the subject; d) retrieving one or more clinical biomarker data; e) detecting an increase in a left atrial volume index (LAVI) within the subject by applying a first decision engine with the extracted P wave parameters from the ECG data and the one or more clinical biomarker data; f) determining a risk score for atrial fibrillation (AF) development in the subject based on the detected increase in the LAVI and one or more subject health parameters; and g) determining the cardiac health status based on the AF risk score; wherein the cardiac health status comprises i) a detected first cardiac condition, ii) a calculated risk score for developing the first cardiac condition by the subject, iii) a change from a previous cardiac health status, or iv) any combination thereof.

In some embodiments, determining the AF risk score comprises applying a second decision engine with the detected increase in the LAVI and the one or more subject health parameters. In some embodiments, determining the cardiac health status comprises applying a third decision engine with the AF risk score.

In some embodiments, the first cardiac condition comprise a cardiac disease. In some embodiments, the first cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof.

In some embodiments, the first decision engine, the second decision engine, and/or the third decision engine comprises a trained model, a decision tree, an analytical expression, or a combination thereof.

In some embodiments, the subject health parameters comprise the one or more clinical biomarker data, one or more imaging data, one or more clinical data, or a combination thereof. In some embodiments, the clinical biomarker data comprise one or more of B-type natriuretic peptide (BNP), N-terminal (NT)-pro hormone BNP (NT-proBNP), and cardiac troponin. In some embodiments, the one or more imaging data comprises one or both of an echocardiogram image and a cardiac MRI. In some embodiments, the one or more clinical parameters comprises, the subject's age, sex, weight, body mass index, height, physiological data, exercise testing results, heart rate, activity levels, velocity, sleep data, or a combination thereof. In some embodiments, the previous ECG data is based on ECG data recorded temporally prior to obtaining the ECG data in step (a). In some embodiments, the ECG device comprises a 12-lead device, a 6-lead device, a 1-lead device, or a 2-lead device. In some embodiments, the ECG device comprises a wearable device.

In some embodiments, the one or more p wave parameters comprise p wave maximal width, variability in p wave width, p wave maximal area, variability in p wave area, and/or p wave slopes. In some embodiments, the one or more P wave parameters are combined with measures of QRS and/or T wave changes.

Disclosed herein, in some aspects, is a method for determining a cardiac health status for a subject, the method comprising: a) obtaining electrocardiogram (ECG) data captured from the subject via an ECG device; b) extracting one or more P wave parameters associated with the ECG data; c) identifying one or more changes in the extracted P wave parameters from previous ECG data of the subject; d) retrieving one or more clinical biomarker data; e) detecting an increase in a left atrial volume index (LAVI) within the subject by applying a first decision engine with the extracted P wave parameters from the ECG data and the one or more clinical biomarker data; f) determining a risk score for atrial fibrillation (AF) development in the subject based on the detected increase in the LAVI and one or more subject health parameters; and g) determining the cardiac health status based on the AF risk score; wherein the cardiac health status comprises i) a detected first cardiac condition, ii) a calculated risk score for developing the first cardiac condition by the subject, iii) a change from a previous cardiac health status, or iv) any combination thereof.

In some embodiments, determining the AF risk score comprises applying a second decision engine with the detected increase in the LAVI and the one or more subject health parameters. In some embodiments, determining the cardiac health status comprises applying a third decision engine with the detected increase in the LAVI and the one or more subject health parameters.

In some embodiments, the first cardiac condition comprises a cardiac disease. In some embodiments, the first cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof.

In some embodiments, the first decision engine, the second decision engine, and/or the third decision engine comprises a trained model, a decision tree, an analytical expression, or a combination thereof.

In some embodiments, the subject health parameters comprise the one or more clinical biomarker data, one or more imaging data, one or more clinical data, or a combination thereof. In some embodiments, the clinical biomarker data comprise one or more of B-type natriuretic peptide (BNP), N-terminal (NT)-pro hormone BNP (NT-proBNP), and cardiac troponin. In some embodiments, the one or more imaging data comprises one or both of an echocardiogram image and a cardiac MRI. In some embodiments, the one or more clinical parameters comprises, the subject's age, sex, weight, body mass index, height, physiological data, exercise testing results, heart rate, activity levels, velocity, sleep data, or a combination thereof. In some embodiments, the previous ECG data is based on ECG data recorded temporally prior to obtaining the ECG data in step (a). In some embodiments, the ECG device comprises a 12-lead device, a 6-lead device, a 1-lead device, or a 2-lead device. In some embodiments, the ECG device comprises a wearable device.

In some embodiments, the one or more p wave parameters comprise p wave maximal width, variability in p wave width, p wave maximal area, variability in p wave area, and/or p wave slopes. In some embodiments, the one or more P wave parameters are combined with measures of QRS and/or T wave changes.

Disclosed herein, in some aspects, is a system for determining a cardiac health status for a subject, the system comprising: a) one or more processors; and b) one or more memories storing instructions that, when executed by the one or more processors, cause the system to perform operations including: 1) obtaining electrocardiogram (ECG) data captured from the subject via an ECG device; 2) extracting one or more P wave parameters associated with the ECG data; 3) identifying one or more changes in the extracted P wave parameters from previous ECG data of the subject; 4) retrieving one or more clinical biomarker data; 5) detecting an increase in a left atrial volume index (LAVI) within the subject by applying a first decision engine with the extracted P wave parameters from the ECG data and the one or more clinical biomarker data; 6) determining a risk score for atrial fibrillation (AF) development in the subject based on the detected increase in the LAVI and one or more subject health parameters; and 7) determining the cardiac health status by applying a second decision engine based on the AF risk score; wherein the cardiac health status comprises i) a detected first cardiac condition, ii) a calculated risk score for developing the first cardiac condition by the subject, iii) a change from a previous cardiac health status, or iv) any combination thereof.

In some embodiments, determining the AF risk score comprises applying a second decision engine with the detected increase in the LAVI and the one or more subject health parameters. In some embodiments, determining the cardiac health status comprises applying a third decision engine with the AF risk score.

In some embodiments, the first cardiac condition comprise a cardiac disease. In some embodiments, the first cardiac condition comprises cardiomyopathy, hypertrophic cardiomyopathy, pulmonary arterial hypertension, amyloid cardiomyopathy, reduced ejection fraction heart failure, arrhythmia (which can include atrial fibrillation), heart failure, heart attack, stroke, myocardial ischemia (including macrovascular and/or microvascular), left atrial myopathy, diastolic dysfunction, or any combination thereof. In some embodiments, the first decision engine, the second decision engine, and/or the third decision engine comprises a trained model, a decision tree, an analytical expression, or a combination thereof.

In some embodiments, the subject health parameters comprise the one or more clinical biomarker data, one or more imaging data, one or more clinical data, or a combination thereof. In some embodiments, the clinical biomarker data comprise one or more of B-type natriuretic peptide (BNP), N-terminal (NT)-pro hormone BNP (NT-proBNP), and cardiac troponin. In some embodiments, the one or more imaging data comprises one or both of an echocardiogram image and a cardiac MRI. In some embodiments, the one or more clinical parameters comprises, the subject's age, sex, weight, body mass index, height, physiological data, exercise testing results, heart rate, activity levels, velocity, sleep data, or a combination thereof. In some embodiments, the previous ECG data is based on ECG data recorded temporally prior to obtaining the ECG data in step (a). In some embodiments, the ECG device comprises a 12-lead device, a 6-lead device, a 1-lead device, or a 2-lead device. In some embodiments, the ECG device comprises a wearable device.

In some embodiments, the one or more p wave parameters comprise p wave maximal width, variability in p wave width, p wave maximal area, variability in p wave area, and/or p wave slopes. In some embodiments, the one or more P wave parameters are combined with measures of QRS and/or T wave changes.

BRIEF DESCRIPTION OF THE DRAWINGS

These and other features, aspects, and advantages of some embodiments will become better understood with regard to the following description and accompanying drawings.

Figure (FIG.) 1 depicts a system environment overview for determining a cardiac health status, in accordance with an embodiment.

DETAILED DESCRIPTION

I. Definitions

Figure 1:
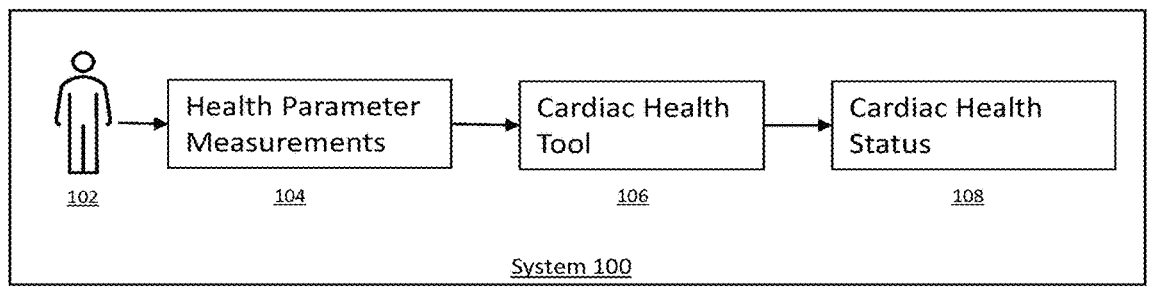

Terms used in the claims and specification are defined as set forth below unless otherwise specified.

The terms "subject" or "patient" are used interchangeably and encompass a cell, tissue, or organism, human or non-human, whether in vivo, ex vivo, or in vitro, male or female.

The terms "treating," "treatment," or "therapy" may be used interchangeably.

It must be noted that, as used in the specification, the singular forms "a," "an" and "the" include plural referents unless the context clearly dictates otherwise.

The terms "ambulatory", "ambulatory measurement", "ambulatory monitoring", "ambulatory monitoring parameters," etc. refer to obtaining health data (e.g., subject health parameters, as described herein) outside a hospital or other medical location (e.g., outside a medical clinic). For example, ambulatory monitoring may refer to monitoring health data (e.g., electrocardiogram, blood pressure, weight, etc.) at home.

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of."

II. System Environment Overview

Described herein, in some embodiments, are systems and methods for detecting, monitoring, and managing a cardiac health status for a subject using ECG data. Figure (FIG.) 1 depicts an overview of an exemplary system 100 for detecting, monitoring, and managing a cardiac health status for a subject 102. In some embodiments, the system 100 receives health parameter measurements 104 from one or more devices that are then used by a cardiac health tool (CHT) 106 to determine a cardiac health status 108. Exemplary health parameter measurements include electrocardiogram (ECG) data from an ECG device and/or weight (from a weight scale for example). As described herein, in some embodiments, determining the cardiac health status includes a) detecting a cardiac condition in the subject, b) predicting a risk of a subject developing a cardiac condition ("cardiac condition risk"), and/or c) temporal monitoring of a cardiac health status for a subject (for example, detecting and/or monitoring for a change in a cardiac condition based on a previous cardiac health status determination). In some embodiments, the cardiac health tool is configured to determine the efficacy of a treatment or therapy applied to reduce the severity and/or risk of a cardiac condition.

As described herein, cardiac condition refers to any cardiac defect, heart failure, or other heart condition. In some embodiments, cardiac condition refers, without limitation, to cardiomyopathy, hypertrophic cardiomyopathy, pulmonary arterial hypertension, amyloid cardiomyopathy, reduced ejection fraction heart failure, arrhythmia (which can include atrial fibrillation, non-sustained ventricular tachycardia (NSVT), etc.), heart failure, heart attack, stroke, myocardial ischemia (including macrovascular and/or microvascular), left atrial enlargement, left atrial myopathy, diastolic dysfunction, or any combination thereof.

Figure 11A:
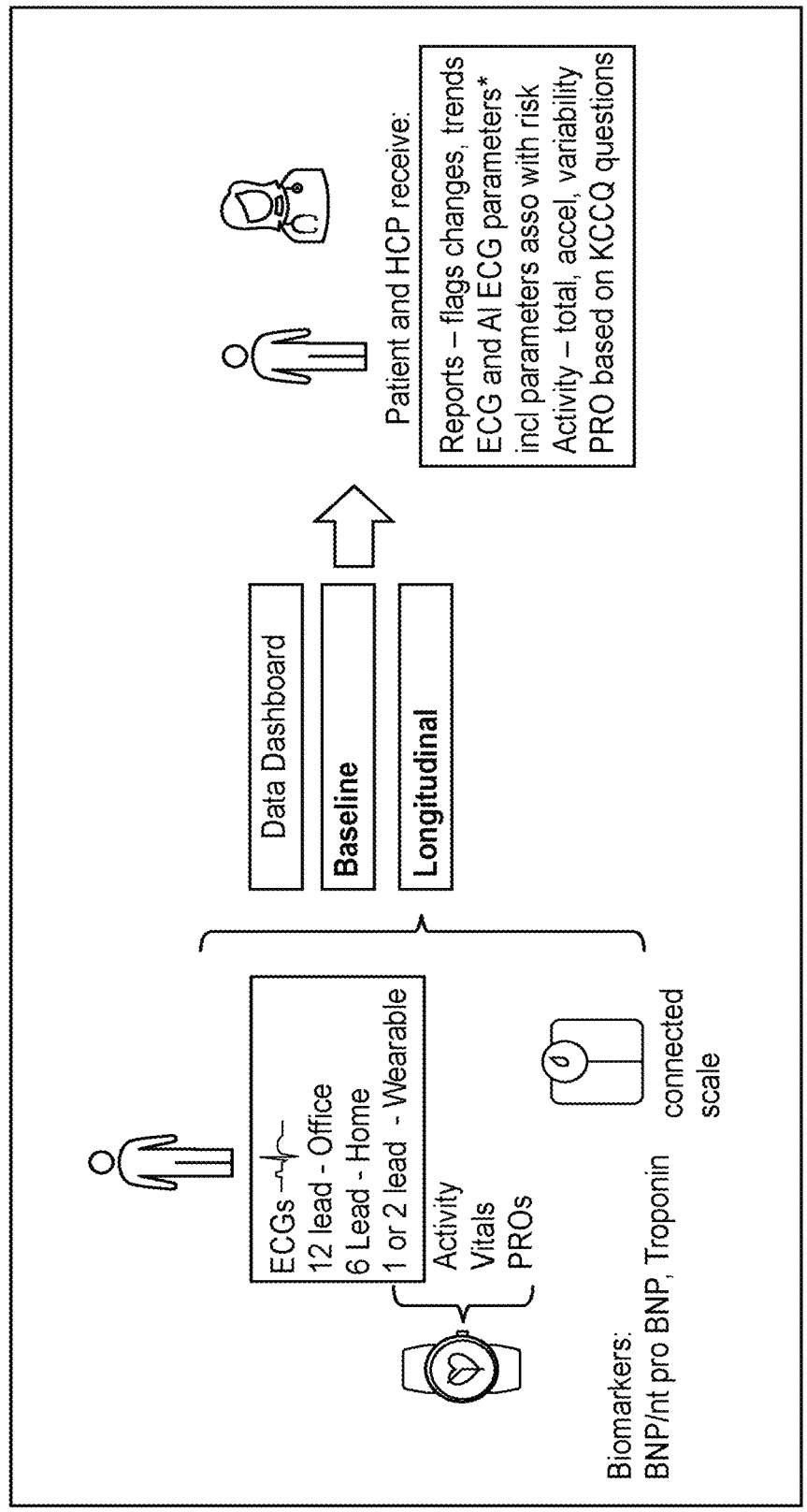
FIG. 11A depicts an exemplary illustration of a system for determining a cardiac health status, in accordance with an embodiment.
Figure 11B:
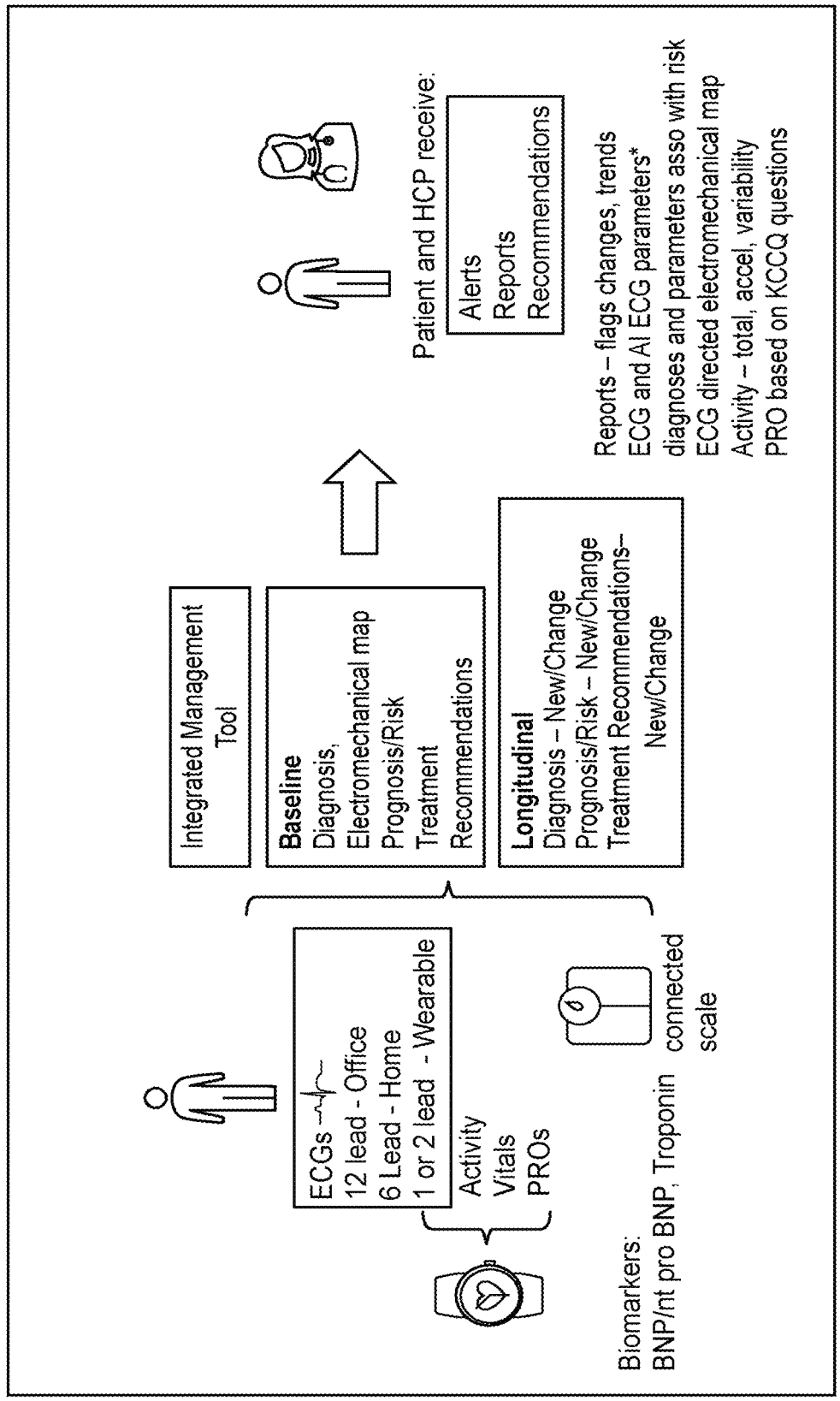
FIG. 11B depicts another exemplary illustration of a system for determining a cardiac health status, in accordance with an embodiment.

In some embodiments, the system 100 provides an integrated management tool for monitoring and managing a cardiac health status for the subject, and for communicating to the subject and/or a healthcare provider (e.g., physician, nurse, or any other medical professional) the cardiac health status, alerts, and/or recommendations. FIGS. 11A-11B provide an exemplary schematic of the health parameters obtained from a subject for establishing a baseline evaluation (e.g., initial cardiac health status), and subsequent measurements used for longitudinal analyses to identify changes in cardiac health status, and to provide alerts, reports, and/or recommendations to the subject and/or healthcare provider.

With reference to FIG. 1, as described herein, the health parameter measurements 104 for a subject 102 (e.g., ECG data from an ECG device) are received by a cardiac health tool 106, which then generates a corresponding cardiac health status 108. In some embodiments, the cardiac health status is output onto a display interface (e.g., a monitor, screen, smart device screen, etc.). As described herein, in some embodiments, the health parameter measurements 104 comprise subject health data obtained via a device or inputted (into a computing device, which may include the system 100) by an individual (e.g., subject, healthcare provider, subject's family/friend, other individual). In some embodiments, wherein the health parameter measurements are obtained via a device, said device and the cardiac health tool 106 are used by different parties. For example, a first party (for example, the subject 102, a medical professional, or any other person) operates an ECG device to obtain the ECG data from the subject 102 (e.g., health parameter measurement 104), wherein the ECG data is then provided to a second party (for example, the subject 102, a medical professional, or any other person different from the individual operating the ECG device) which implements the cardiac health tool 106 to determine a cardiac health status. In some embodiments, the device to obtain the health parameter measurement 104 and the cardiac health tool 106 are used by the same party. Similarly, in some embodiments, wherein the health parameter measurements are obtained via being inputted into a computing device, said inputting and operating the cardiac health tool 106 are performed by the same party or by different parties.

Figure 4:
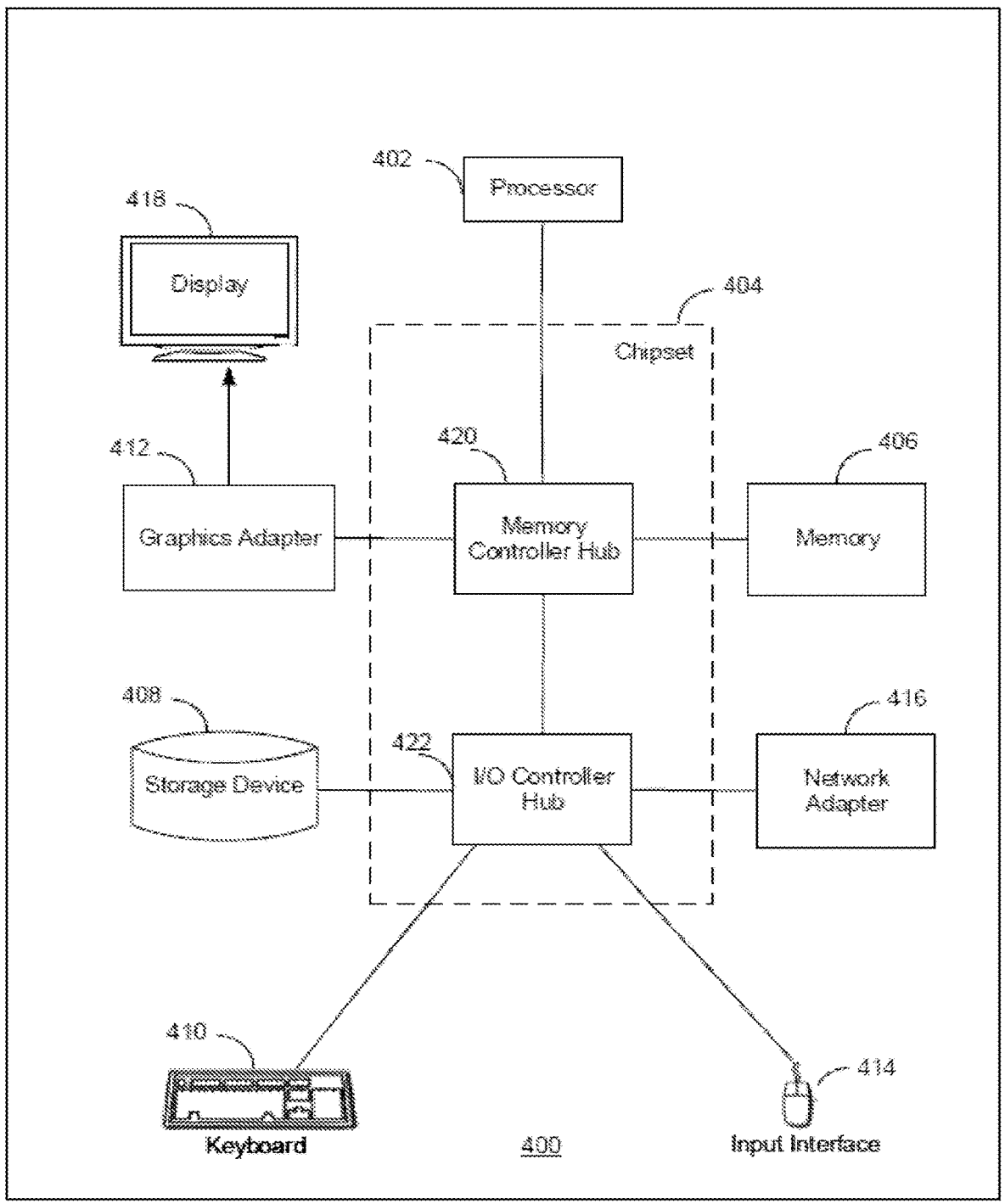
FIG. 4 depicts an exemplary computer system, in accordance with an embodiment.

In some embodiments, the cardiac health tool is provided by one or more computing devices, wherein the cardiac health tool can be embodied as a computer system (e.g., see FIG. 4, reference character 400). Accordingly, in some embodiments, methods and steps described in reference to the cardiac health tool 106 are performed in silico. For example, in some embodiments, the cardiac health tool is configured to apply one or more health parameter measurements to one or more decision engines (e.g., trained models, decision trees, analytical expressions, etc.) so as to determine the cardiac health status. In some embodiments, the one or more decision engines each apply an algorithm, such as a machine learning algorithm (as described herein), to the one or more health parameter measurements.

Figure 2A:
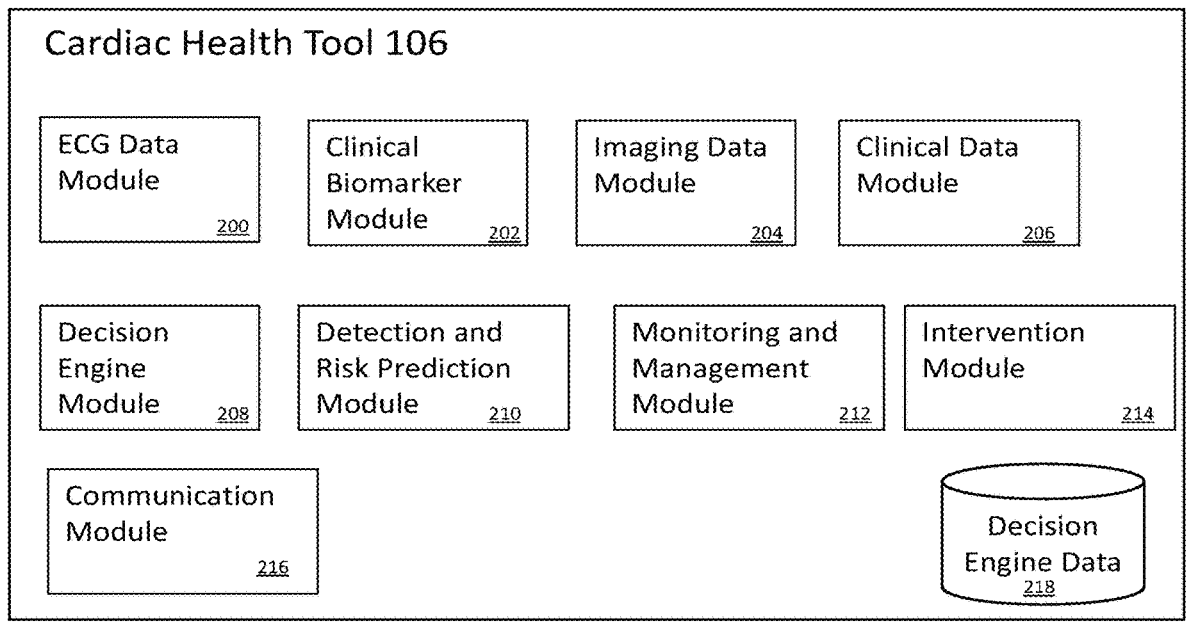
FIG. 2A depicts a block diagram of the cardiac health tool, in accordance with an embodiment.

With reference to FIG. 2A, a block diagram is depicted illustrating exemplary computer logic components of the cardiac health tool 106, in accordance with an embodiment. Here, the cardiac health tool 106 includes an ECG data module 200, a clinical biomarker module 202, an imaging data module 204, a clinical data module 206, a decision engine module 208, a detection and risk prediction module 210, a monitoring and management module 212, an intervention module 214, a communication module 216, and a decision engine data storage 218. In some embodiments, the cardiac health tool 106 can be configured differently with additional or fewer modules. For example, a cardiac health tool 106 need not include the imaging data module 204. In some embodiments, the decision engine module 208 and/or the decision engine data storage 218 are located on a different tool and/or computing device.

As described herein, in some embodiments, the cardiac health tool 106 is configured to determine a cardiac health status 108 for a subject 102. In some embodiments, the cardiac health tool 106 applies health parameters obtained for the subject to one or more decision engines to determine the cardiac health status. In some embodiments, the subject's health parameters are obtained via the ECG data module 200, the clinical biomarker module 202, the imaging data module 204, and/or the clinical data module 206.

Subject Health Parameters

In some embodiments, the ECG data module 200 is configured to be in operative communication with an ECG device for obtaining ECG data from the subject. Accordingly, in some embodiments, the ECG data module is configured to receive ECG data from the ECG device, and optionally extract one or more parameters of the ECG data. The ECG device can be any device known in the art used for obtaining ECG data. For example, in some embodiments, the ECG device comprises a 12-lead ECG device, a 6-lead ECG device, a single lead ECG device, or a double lead ECG device. In some embodiments, the 12-lead ECG device is found at a health location, such as a healthcare provider office or clinic, including a hospital, physician's office, medical clinic, or any other location staffing medical and/or health professionals (e.g., physicians, emergency medical technicians, nurses, first responders, psychologists, phlebotomist, medical physics personnel, nurse practitioners, surgeons, dentists, and any other obvious medical professional as would be known to one skilled in the art). In some embodiments, the ECG device is configured to be used outside a healthcare provider's office or clinic (as described herein). For example, the ECG device can be used by the subject at home (e.g., ambulatory monitoring). In some embodiments, the ECG device, for example a single or double lead ECG device, is incorporated in a wearable device (for example a watch, smartwatch) or other type of mobile device, and thus configured to obtain ECG data while the subject is at rest and/or moving. As used herein, the term "ambulatory monitoring" or "ambulatory measurements" refer to monitoring that occurs and/or measurements that are obtained outside a medical location, such as a hospital or other type of medical location (e.g., a clinic).

In some embodiments, the ECG device (for example a wearable device such as a smartwatch) incorporates its own software (such as a software application, or an "app") to store the raw ECG data obtained by the ECG device, which may include, without limitation, ECG waveforms. In some embodiments, the ECG device software is in operative communication with the ECG data module 200. In some embodiments, the ECG data module 200 includes the software application receiving the raw ECG data.

In some embodiments, the ECG data module is configured to extract specific parameters from the ECG data for detecting a specific cardiac condition and/or risk. In some embodiments, the one or more specific ECG parameters that can be extracted from the ECG data include P wave parameters, PR interval parameters, QRS complex, J-point, ST segment, T wave, corrected QT interval, U wave, or any combination thereof. For example, in some embodiments, one or more decision engines described herein use P wave parameters from ECG data to identify an increase in left atrial volume index or associated increase in diastolic filling pressures. For example, in some cases, ST segment changes correlate with left ventricular (LV) strain related to LV loading pressures and correlate with adverse outcomes. Since loading pressures increase with increased cardiac output demand, it is expected that ST segment changes would be observed with activity at earlier stages of increasing HF risk and ST changes with rest may correlated with higher stages of risk; similar to expected changes in sleeping HR and daily activity (as described herein).

In some embodiments, the ECG data module 200 provides one or more of the ECG parameters to the detection and risk prediction module 210 and/or the monitoring and management module 212. In some embodiments, the detection and risk prediction module 210 and/or the monitoring and management module 212 are configured to extract the one or more ECG parameters from the ECG data received by the ECG data module 200.

In some embodiments, the ECG data is obtained with exercise testing, which help provide important information on potential cardiac ischemia, while ECG data in the ambulatory setting are employed to assess potential rhythm abnormalities.

In some embodiments, the clinical biomarker module 202 is configured to obtain and optionally store data relating to one or more clinical biomarkers in the subject. In some embodiments, the one or more clinical biomarkers comprise one or more blood borne protein measures, one or more blood borne molecular measures, urine protein, and/or one or more other molecular measures. Exemplary blood borne protein measurements include a B-type natriuretic peptide (BNP), N-terminal (NT)-pro hormone BNP (NT-proBNP), cardiac troponin, or a combination thereof. In some embodiments, said data of one or more clinical biomarkers may include an amount, concentration, and/or level of said one or more clinical biomarkers.

Such clinical biomarkers can correlate to several factors for cardiac health. For example, blood borne measures of cardiac wall stress (NT pro BNP) and myocardial injury (troponin) as well as lipid profiles and diabetic parameters (blood glucose and HbA1c) as well as inflammation (hs CRP) are well established in cardiovascular evaluation and management.

In some embodiments, the data of the one or more clinical biomarkers are obtained via a blood sample from the subject, wherein the blood sample is further processed to identify said one or more clinical biomarkers. In some embodiments, the blood sample can be obtained by a healthcare provider (e.g., a medical and/or health professional as described herein), and/or by the subject or a non-medical or non-health professional. In some embodiments, the blood sample can be processed in a laboratory, hospital, medical clinic, health center, or any combination thereof. In some embodiments, the blood sample can be processed using a point of care device, thereby enabling the subject to have the blood sample processed in a non-medical location (for example at home). In some embodiments, the results of the blood sample processing identifies the one or more clinical biomarkers (and relative data, such as amount, concentration and/or level), wherein said results can be inputted or sent to a computing device in operative communication with the clinical biomarker module 202, thereby enabling the clinical biomarker module 202 to receive the one or more clinical biomarkers. In some embodiments, the results of the blood processing are inputted or sent directly to the clinical biomarker module 202.

In some embodiments, the imaging data module 204 is configured to obtain and optionally store images obtained pertaining to the subject. In some embodiments, such images comprise MRI scans (for example, cardiac MRI scans), and/or echocardiogram scans. In some embodiments, the images are sent from a healthcare provider (e.g., from a medical or other healthcare clinic), via a computing device in operative communication with the imaging data module 204. In some embodiments, the subject or other non-medical professional is configured to upload or send the image(s) to be received by the imaging data module 204.

In some embodiments, the imaging data module 204 is configured to extract one or more echocardiography parameters. For example, exemplary left ventricle echocardiography parameters include outflow track obstruction, ejection fraction, fractional shortening, mass index, maximum wall thickness, septal thickness, and/or strain. Exemplary mitral value echocardiography parameters include systolic anterior motion and/or regurgitation. Exemplary left atrium echocardiography parameters include maximal and/or minimal diameter, volume index, ejection fraction, function and/or strain.

Figure 2B:
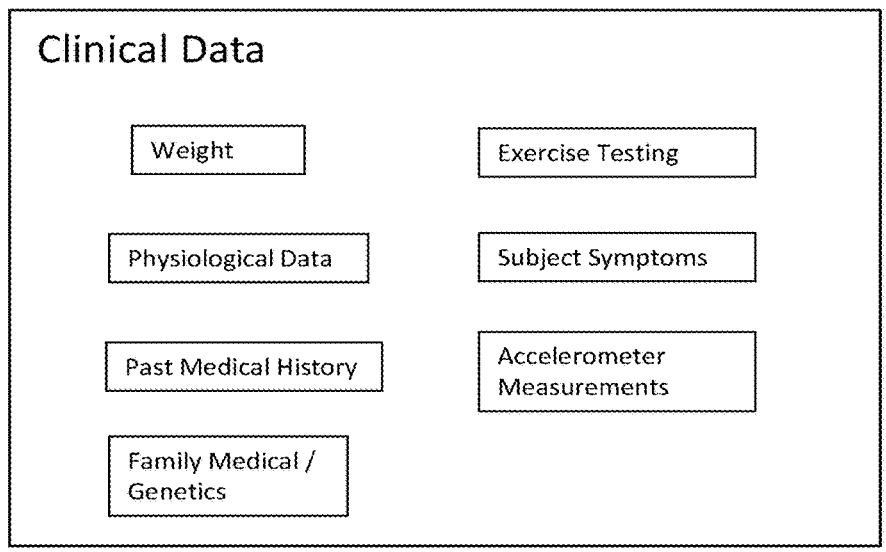
FIG. 2B depicts a block diagram of exemplary clinical data parameters, in accordance with an embodiment.

In some embodiments, the clinical data module 206 is configured to obtain and optionally store one or more clinical parameters. FIG. 2B provide exemplary clinical parameters. For example, in some embodiments, the clinical parameters comprise the subject's age, sex, weight, body mass index, height, etc., In some embodiments, clinical parameters (e.g., weight) are communicated to the clinical data module 206 via a smart device, such as a weight scale in operative communication with the clinical data module 206. In some cases, weight is an important factor for cardiovascular care, both as chronic and acute risk measure. Chronically weight may serve as an indirect correlate of cardiovascular fitness and is often measured in routine clinical practice. In some cases, acute changes in weight are primarily related to fluid and increases may be signs of worsening heart failure. In some cases, daily home weight measures are employed in heart failure management for select patients.

In some embodiments, the clinical parameters include physiological data, e.g., heart rate, blood glucose, blood pressure, respiration rate, body temperature, blood volume, blood oxygen saturation, etc. In some embodiments, such physiological data is obtained via a smart device, such as a wearable device or other device configured to be in operative communication with the clinical data module 206. For example, in some cases, clinical parameters comprise heart rate measurements, such as while a subject is asleep. In some cases, increased sleeping heart rate is correlated with an increase in heart failure risk. For example in some cases, increased sleeping heart rate is physiologically related to reductions in basal cardiac function, stroke volume, and prior to a reduction in cardiac output that may lead to a heart failure admission.

In some embodiments, the clinical parameters comprise subject exercise results, subject activity (for example, fitness activity or other movement), velocity, sleep data, etc. In some embodiments, such clinical parameters are obtained via a smart device, such as a wearable device or other device configured to be in operative communication with the clinical data module 206. For example, in some embodiments, an accelerometer is used to provide such clinical parameters. In some cases, a reduced daily activity correlates with an increased heart failure risk, due to the potential for affecting the ability of the subject to increase cardiac output.

In some embodiments, exercise testing is important in assessing cardiopulmonary conditions. In some embodiments, exercise testing measurements include maximal exercise in power (METs/Watt) and distance (for example, a six minute walk). In some embodiments, maximal exercise testing on a treadmill or stationary cycle is conducted in combination with ECG monitoring and often with an imaging to assess cardiac function and/or ischemia. In some embodiments, distance testing is conducted on a defined course under supervision with or without ECG monitoring. Connected consumer wearable technologies are well established in their ability to measure multiple ambulatory activity parameters including total steps, velocity and duration. These data can be adapted to provide clinical insights similar to supervised exercise protocols, especially when integrated ECG and other ambulatory data.

In some embodiments, any one of such clinical parameters can be inputted by the subject and/or a health care provider.

In some embodiments, the clinical parameters include other data that can be inputted by the subject and/or healthcare provider, or transmitted from a healthcare provider. For example, such other data can include reported symptoms by the subject, past medical history, current and/or past medications, family medical history, genetics, or any combination thereof.

In some embodiments, the assessment of symptoms is an important factor for cardiovascular care. In some embodiments, symptoms are primarily recorded during patient encounters while patients/families may notify healthcare providers to changes/lack of changes ad hoc. In some cases, symptom logs are not commonly employed outside of the specific testing protocols or the clinical trial setting. As described herein, in some embodiments, the cardiac health tool 106 is configured to receive inputting of symptoms by the subject, healthcare provider, or other individual.

Connected consumer wearable technologies are well suited to prompt individuals to input the symptoms with both structured and open fields. These inputs can be integrated with other ambulatory inputs, providing a longitudinal record of symptoms with associated clinical parameters.

Decision Engine(s) and Decision Engine Data

In some embodiments, the decision engine module 208 applies one or more algorithms to determine a cardiac health status based on ECG data, clinical biomarkers, imaging data, and/or clinical data parameters (as described herein). In some embodiments, each algorithm may correspond to identifying a specific cardiac health status for the subject, such as a specific cardiac condition, and/or a risk calculation for a cardiac condition in the subject. In some embodiments, the one or more decision engines apply algorithms (e.g., algorithms embodied in trained models) to correlate the various combinations of health parameters of the subject with a cardiac health status. In some embodiments, at least one of the one or more algorithms may comprise a machine learning algorithm incorporating artificial intelligence (AI) to help improve accuracy of said cardiac health status determination. For example, in some embodiments, said artificial intelligence is applied to trained model data (which may be included in the decision engine data) and optionally existing cardiac health status data (such as specific ECG data correlating with a cardiac condition) to identify the parameters for detecting a cardiac health status, thereby training the model.

In some embodiments, any one of the decision engine(s) described herein is any one of a regression model (e.g., linear regression, logistic regression, or polynomial regression), decision tree, random forest, gradient boosted machine learning model, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks), or any combination thereof. In particular embodiments, any one of the decision engine(s) described herein is a logistic regression model. In particular embodiments, any one of the decision engine(s) described herein is a random forest classifier. In particular embodiments, any one of the decision engine(s) described herein is a gradient boosting model.

In some embodiments, any one of the decision engine(s) described herein (e.g., a trained model) can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, and dimensionality reduction techniques such as manifold learning, principal component analysis, factor analysis, autoencoder regularization, and independent component analysis, or combinations thereof. In particular embodiments, the machine learning implemented method is a logistic regression algorithm. In particular embodiments, the machine learning implemented method is a random forest algorithm. In particular embodiments, the machine learning implemented method is a gradient boosting algorithm, such as XGboost. In some embodiments, any one of the trained model(s) described herein is trained using supervised learning algorithms, unsupervised learning algorithms, semi-supervised learning algorithms (e.g., partial supervision), weak supervision, transfer, multi-task learning, or any combination thereof.

In some embodiments, any one of the trained model(s) described herein has one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, node values in a decision tree, and coefficients in a regression model. The model parameters of the risk prediction model are trained (e.g., adjusted) using the training data to improve the predictive capacity of the risk prediction model.

In some embodiments, any one of the trained model(s) described herein are trained via training data located in the trained model data (which may be included with the decision engine module 218).

In various embodiments, the training data used for training any one of the trained model(s) described herein includes reference ground truths that indicate that a training individual was diagnosed with a cardiac condition, or diagnosed within a time period (hereafter also referred to as "positive" or "+") or whether the training individual was not diagnosed with the cardiac condition (hereafter also referred to as "negative" or "−"). In various embodiments, the reference ground truths in the training data are binary values, such as "1" or "0." For example, a training individual that was diagnosed with a cardiac condition can be identified in the training data with a value of "1" whereas a training individual that was not diagnosed with a cardiac condition within the time period can be identified in the training data with a value of "0." In various embodiments, any one of the trained model(s) described herein are trained using the training data to minimize a loss function such that any one of the trained model(s) described herein can better predict the outcome (e.g., future diagnosis of a cardiac condition) based on the input (e.g., extracted features of the subject's health parameters). In some embodiments, the loss function is constructed for any of a least absolute shrinkage and selection operator (LASSO) regression, Ridge regression, or ElasticNet regression. In some embodiments, any one of the trained model(s) described herein is a random forest model, and is trained to minimize one of Gini impurity or Entropy metrics for feature splitting, thereby enabling any one of the trained model(s) described herein to more accurately detect a cardiac condition and/or the risk of a cardiac condition in the subject.

In various embodiments, the training data can be obtained and/or derived from a publicly available database. In some embodiments, the training data can be obtained and collected independent of publicly available databases. Such training data can be a custom dataset.

In some embodiments, cardiac health status data as obtained via the system 100 is stored in the decision engine data storage 218. In some embodiments, decision engine data storage includes ranges and/or combinations that correlate the subject data (e.g., ECG data, imaging, clinical biomarkers, subject health parameters) with a particular cardiac health status (e.g., cardiac condition). For example, in some cases, certain ECG parameters correlate with conditions related to hypertrophic cardiomyopathy (HCM) risk, such as p wave parameters and changes associated with left atrial enlargement, and QRS changes linked to pulmonary hypertension, such that a decision engine incorporating such ECG parameters with other ECG correlations and other measures of risk (such as nt pro BNP, troponin, left ventricular mass, ejection fraction, etc.), which may be obtained via the decision engine data storage 212, provide a measure of risk to those with HCM and other cardiomyopathies. In some embodiments, the decision engine data storage 212 is updated via communication with an external database, and/or is updated based on subject health parameters as received from the subject.

Cardiac Condition Detection and Risk Prediction

Cardiac Condition Detection

In some embodiments, as described herein, the detection and risk prediction (DRP) module 210 is configured to correlate the subject's health parameters (as described herein) with a cardiac condition, via the one or more decision engines, so as to detect a cardiac condition in the subject, and optionally, a severity of the cardiac condition in the subject. In some embodiments, the DRP module 210 is configured to access one or more trained modules for a given cardiac condition. For example, in some embodiments, the DRP module 210 accesses one or more decision engines correlating to hypertrophic cardiomyopathy (HCM), wherein the corresponding subject's health parameters (per the latest measurements) are applied and determined whether the correlation identifies with HCM. In some cases, the decision engine(s) may include specific permutation of the health parameters (including specific threshold levels) that identify a specific type of cardiomyopathy such as HCM, amyloid, pulmonary atrial hypertension, atrial and ventricular cardiomyopathies.

In some embodiments, a cardiac condition is detected based on a detection of one or more other cardiac conditions by the DRP module 210, and/or based on a risk score of one or more other cardiac conditions. For example, in some embodiments, the DRP module 210 detects a first cardiac condition based on one or more decision engines and one or more of the subject's health parameters obtained. In some embodiments, the DRP module 210 is configured to apply one or more decision engines (some of which may be the same from detection of the first cardiac condition) with one or more health parameters of the subject, so as to detect a second cardiac condition. In some embodiments, the DRP module 210 is configured to determine a risk score for a second cardiac condition (as described herein), based on the detection of the first cardiac condition, wherein the DRP module 210 is then configured to apply one or more decision engines (some of which may be the same from detection of the first cardiac condition) with one or more health parameters of the subject and the risk score for the second cardiac condition, so as to detect a third cardiac condition in the subject.

For example, in some embodiments, one or more decision engines (as described herein) are configured to detect left atrial enlargement based on the ECG data obtained and optionally, based on one or more other health parameters, such as clinical biomarkers (e.g., NT-proBNP). In some embodiments, the DRP module 210 correlates the identified left atrial enlargement with diastolic dysfunction (an exemplary cardiac condition), which relates to impaired filling of the left atrium. In some embodiments, the subject's health parameters, such as symptoms inputted by the subject are also considered by the DRP module 210 in detecting and/or diagnosing diastolic dysfunction and/or left atrial enlargement in the subject.

As described herein, in another exemplary embodiment, the DRP module 210 is configured to determine a risk of the subject developing atrial fibrillation (AF) based on detection of left atrial enlargement or measures correlated with increased diastolic filling pressures in the subject, which may be via a decision engine and/or through successive cardiac health status determinations (e.g., via the monitoring and management module 212). In some embodiments, these parameters may include increased or increasing p wave maximal width, variability in p wave width, p wave maximal area, variability in p wave area, or p wave slopes. P wave parameters may be combined with measures of QRS and T wave changes. AF risk may be correlated with rate of P wave or QRS or T wave parameter change over time. Correlations with AF risk may be specific to specific cardiovascular conditions, such as specific cardiomyopathy diagnosis. In some embodiments, a risk score is associated with AF for the subject. Accordingly, in some embodiments, the DRP module 210 is configured to detect and/or diagnose cardiomyopathy in the subject based on the identified risk of AF in the subject, and optionally in consideration of one or more of the subject's health parameters (e.g., ECG data, biomarkers, subject health data).

As described herein, the DRP module 210 may detect a first cardiac condition using a first decision engine, which is then used with a second decision engine to identify a second cardiac condition. In some embodiments, the DRP module 210 further determines a state of the cardiac condition (for example a severity state), and assigns a score relating to the severity of the cardiac condition.

Risk Prediction

In some embodiments, as described herein, the DRP module 210 is configured to determine a risk of the subject developing or experiencing a cardiac condition. In some embodiments, the DRP module 210 is configured to apply one or more decision engines with one or more of the subject's health parameters (as described herein) to identify a risk of the subject developing and/or experiencing a cardiac condition. As described herein, the DRP module 210 may detect a first cardiac condition in the subject, or a risk of the first cardiac condition, using a first decision engine, which is then used with a second decision engine to determine a risk of a second cardiac condition developing or being experienced by the subject. In some embodiments, the risk of a cardiac condition is correlated with a risk score.

As described herein, in some embodiments, the DRP module 210 correlates the identification of a cardiac condition (e.g., left atrial enlargement via the cardiac condition detection module) with a risk for atrial fibrillation in the subject. In some embodiments, the DRP module 210 detects a specific cardiomyopathy in the subject based on the ECG data, and optionally other health factors of the subject (as described herein). In some embodiments, the DRP module 210 is then configured to correlate the ECG data with the left atrial enlargement detection, and in some cases detection of a specific cardiomyopathy, to determine a risk score for another cardiac condition, such as atrial fibrillation, stroke, and/or sudden death, in the subject. Accordingly, in some embodiments, the system 100 is configured not only to detect atrial fibrillation in a subject, but also detect the risk of the subject developing atrial fibrillation, and thereby associating a risk to other cardiac conditions (for example, that may result due to atrial fibrillation). In some embodiments, said correlation of ECG data, the left atrial enlargement, and/or the specific cardiomyopathy is via a decision engine.

In some embodiments, the DRP module 210 is configured to determine or revise a risk score for a cardiac condition based on changes to health parameters for the subject. For example, in some embodiments, changes in ECG data and subject health data are provided via the monitoring and management module 212 according to a temporal frequency or via sporadic measurements, thereby enabling for monitoring of a cardiac health status (as described herein). For example, in some embodiments, revised ECG data and other physiological data are obtained on a daily basis, thereby enabling for a risk score for a cardiac condition to be monitored with daily updates to the subject's health parameters.

Accordingly, in some embodiments, the DRP module 210 and monitoring and management module 212 enable the monitoring of progression or recession of cardiac conditions in the subject. For example, in some cases, development of atrial fibrillation in a subject is a major contributor to both cardiomyopathy and heart failure associated risks and disease progression, and thus identifying a risk of atrial fibrillation (including a change to a risk score) enables for a monitoring of cardiomyopathy and/or heart failure associated risks and/or disease progression. In some cases, as described herein, a risk of atrial fibrillation in a subject can be determined by correlating ECM data with left atrial enlargement, which is a factor for atrial fibrillation development.

In some embodiments, left atrial volume index (LAVI) is also a predictor of atrial fibrillation, wherein an increase in the LAVI of a subject can correlate to an atrial fibrillation risk. As used herein, in some cases, an increase in left atrial volume index correlates with left atrial enlargement. For example, atrial fibrillation risk is mechanistically linked to increased left atrial volumes, which increase with increased left ventricle filling pressures that are common in cardiomyopathies and heart failure. Accordingly, in some cases, an increase in LAVI correlates to cardiomyopathy and/or heart failure progression (for example, heart failure with preserved ejection fraction). Left atrial dimensions are directly measured with imaging such as echocardiography, but in some cases, the ECG p wave provides robust correlation with atrial parameters. In some cases, the P wave measures in ECG data, along with other health parameters of the subject can be correlated with the LAVI and one or more clinical biomarkers (e.g., nt pro BNP). For example, in some cases, an increase in P wave parameters (from ECG data)

can be correlated to an increase in LAVI, and/or other measures of left atrial function (for example, as identified via echocardiography parameters as described herein). Other exemplary measures of left atrial function include left atrial ejection fraction and/or strain patterns.

Accordingly, in some embodiments, the DRP module 210, using one or more decision engines, is configured to correlate changes in P wave parameters with cardiomyopathy and/or heart failure progression. In some embodiments, the P wave parameters include increased or increasing p wave maximal width, variability in p wave width, p wave maximal area, variability in p wave area, and/or p wave slopes. In some embodiments, P wave parameters are combined with measures of QRS and T wave changes. In some embodiments, atrial fibrillation (AF) risk is correlated with rate of P wave or QRS or T wave parameter change over time. Correlations with AF risk may be specific to specific cardiovascular conditions, such as specific cardiomyopathy diagnosis. In some embodiments, the one or more decision engines consider one or more health parameters of the subject in addition to changes in P wave parameters to correlate cardiomyopathy and/or heart failure progression (decline). For example, in some embodiments, the one or more decision engines include health parameters obtained from an accelerometer, which may include parameters for daily activity measures, velocity, and/or variability. In some embodiments, the one or more decision engines are configured for cardiomyopathy and/or heart failure in general, or can be further specified for a specific type of cardiomyopathy and/or heart failure.

In other embodiments, the P wave parameters are not considered by the one or more decision engines in detecting cardiomyopathy and/or heart failure, including progression or regression of cardiomyopathy and/or heart failure (instead other health parameters are considered).

As described herein, in some embodiments, the changes to P wave parameters are based on changes obtained via the monitoring and management module 210, wherein ECG data may be obtained according to a temporal frequency (such as daily, weekly, etc.). In some embodiments, temporal changes between previous measurement readings may include absolute changes and/or relative changes. In some embodiments, the rate of change of the P wave parameter versus time is also considered by the one or more decision engines.

In some embodiments, at least some of the decision engines are configured to detect a progression in a cardiac condition through comparison with health parameters for subjects that are not diagnosed with the cardiac condition. For example, in some embodiments, a decision engine for a given cardiac condition, such as hypertrophic cardiomyopathy (HCM), may identify larger changes from health parameters for non-HCM subjects (for example, larger changes or deviations in ECG parameters as compared to a non-HCM subject) as correlating to more severe conditions of HCM as opposed to smaller changes (compared to the non-HCM subject), which may correlate to less severe conditions of HCM.

Monitoring and Management of a Cardiac Health Status

In some embodiments, the monitoring and management (MM) module 212 is configured to monitor the cardiac health status of a subject via periodic measurement and input of health parameters. For example, in some embodiments, the MM module 212, in communication with a device configured to provide a health parameter, such as an ECG device or an accelerometer, is configured to obtain data from such devices and send to the DRP module 210 for revised determinations relating to cardiac condition detection and/or risk prediction of a cardiac condition.

Figure 9A:
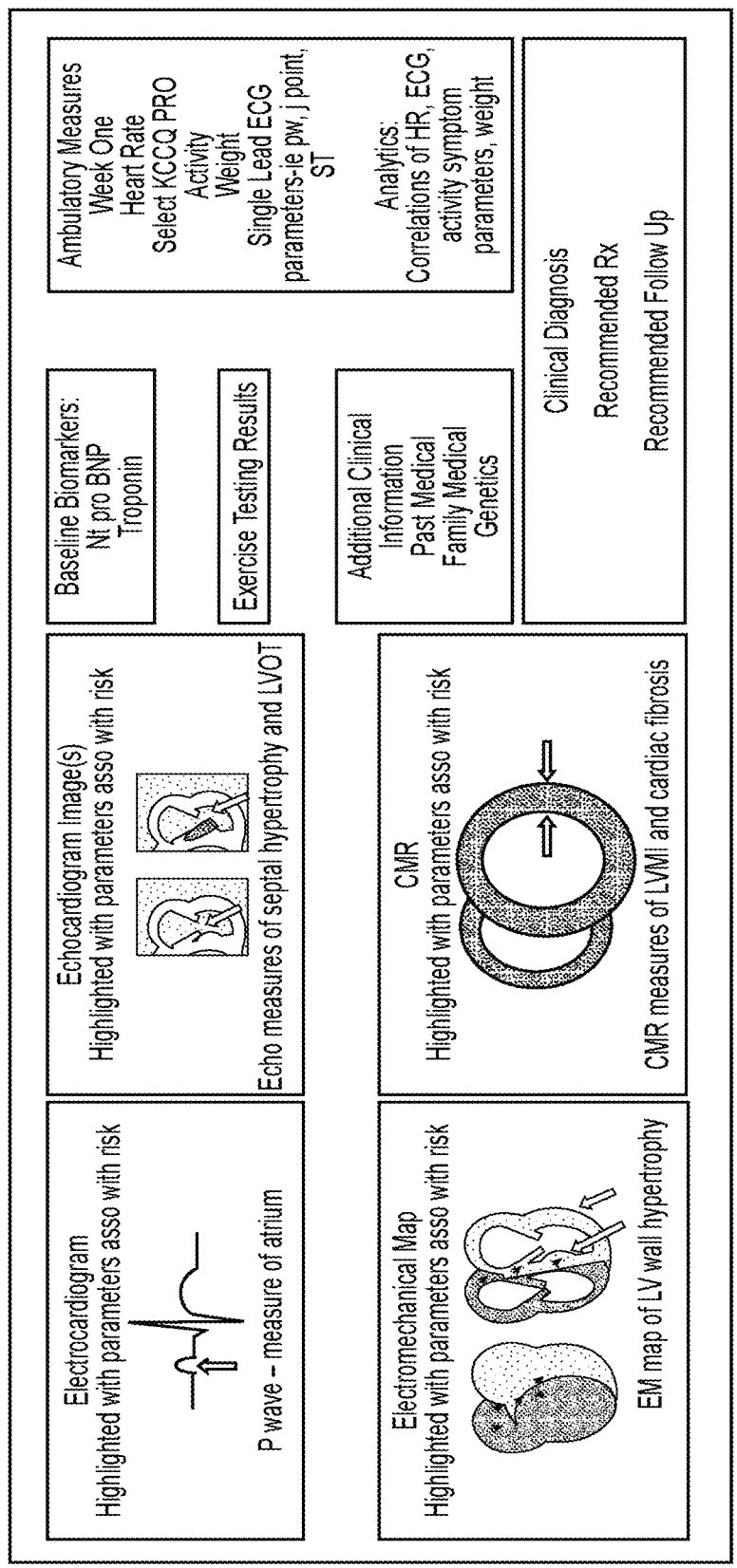
FIG. 9A depicts an exemplary illustration of a baseline evaluation output, in accordance with an embodiment.

In some embodiments, the MM module 212 first establishes a baseline evaluation of the cardiac health status of the subject, based on health parameters initially received by the system 100. FIG. 9 provides an exemplary depiction of an output for a baseline evaluation, identifying several of the health factors that were recorded or inputted to the system 100. In some embodiments, the baseline evaluation is identified with a temporal period (for example "Week One"). As depicted in FIG. 9A, in some embodiments, the relevant health parameters of the subject for performing a baseline evaluation are depicted, such as ECG data, echocardiogram images, an electrochemical map, a cardiac magnetic resonance (CRM) image, clinical biomarkers, exercise testing results, additional clinical information (such as past medical information, current and/or past medications taken by the subject, family medical history, genetics, age, sex, patient report symptoms). In some embodiments, ambulatory measures (e.g., measurements that are obtained outside a hospital or other medical clinic, e.g., at home) are depicted along with the corresponding temporal information (e.g., "week one"). Such ambulatory measurements (e.g., heart rate, select Kansas City Cardiomyopathy Questionnaire (KCCQ PRO), activity, weight, single or double lead ECG parameters, etc.) may provide a benchmark via the temporal stamp (e.g., "week one"). In some embodiments, the MM module 212, in communication with the DRP module 210, is configured to output a preliminary diagnosis of a cardiac condition and/or a prediction of risk score a cardiac condition, such that the baseline evaluation includes said cardiac condition and risk score. In some embodiments, preliminary diagnoses will be reviewed by healthcare professionals. In some embodiments, the baseline evaluation module outputs a recommended intervention or therapy, which may be automatically determined by the system (for example via the intervention module 214), by a medical or health professional, or both.

In some embodiments, the baseline evaluation establishes a benchmark for the subject's health parameters and an initial cardiac health status for future monitoring of the cardiac health status of the subject 102 by the system 100 (e.g., via longitudinal analysis), wherein changes in health parameters, as compared with the baseline evaluation may be indicative of increasing or decreasing risk of a subject developing a cardiac condition (as described herein).

For example, as described herein, the MM module 212 is configured to monitor the cardiac health status of the subject via periodic retrieval of some of the health parameters (as described herein) at a prescribed frequency, so as to identify changes to a cardiac health status in a patient, as compared to the baseline evaluation and/or past cardiac health statuses. In some embodiments, the prescribed frequency includes any temporal frequency prescribed by the subject, a medical professional, or other individual. For example, in some embodiments, the prescribed frequency includes obtaining one or more health parameters daily, every 2, 3, 4, 5, or 6 days, weekly, bi-weekly, monthly, every 4 to 20 weeks, etc. In some embodiments, the MM module 212 is configured to identify a) changes to subject's health parameters, from a previous measurement (e.g., longitudinal changes in the subject data), b) changes to the detected cardiac condition(s) in a subject and/or a cardiac condition severity (for example, via the DRP module 210 as described herein), c) changes to a risk score for a cardiac condition (for example, via the DRP module 210 as described herein), d) efficacy of a treatment or therapy for a cardiac condition or risk of cardiac condition (for example via the intervention module 214, as described herein), or e) any combination thereof.

Figure 9B:
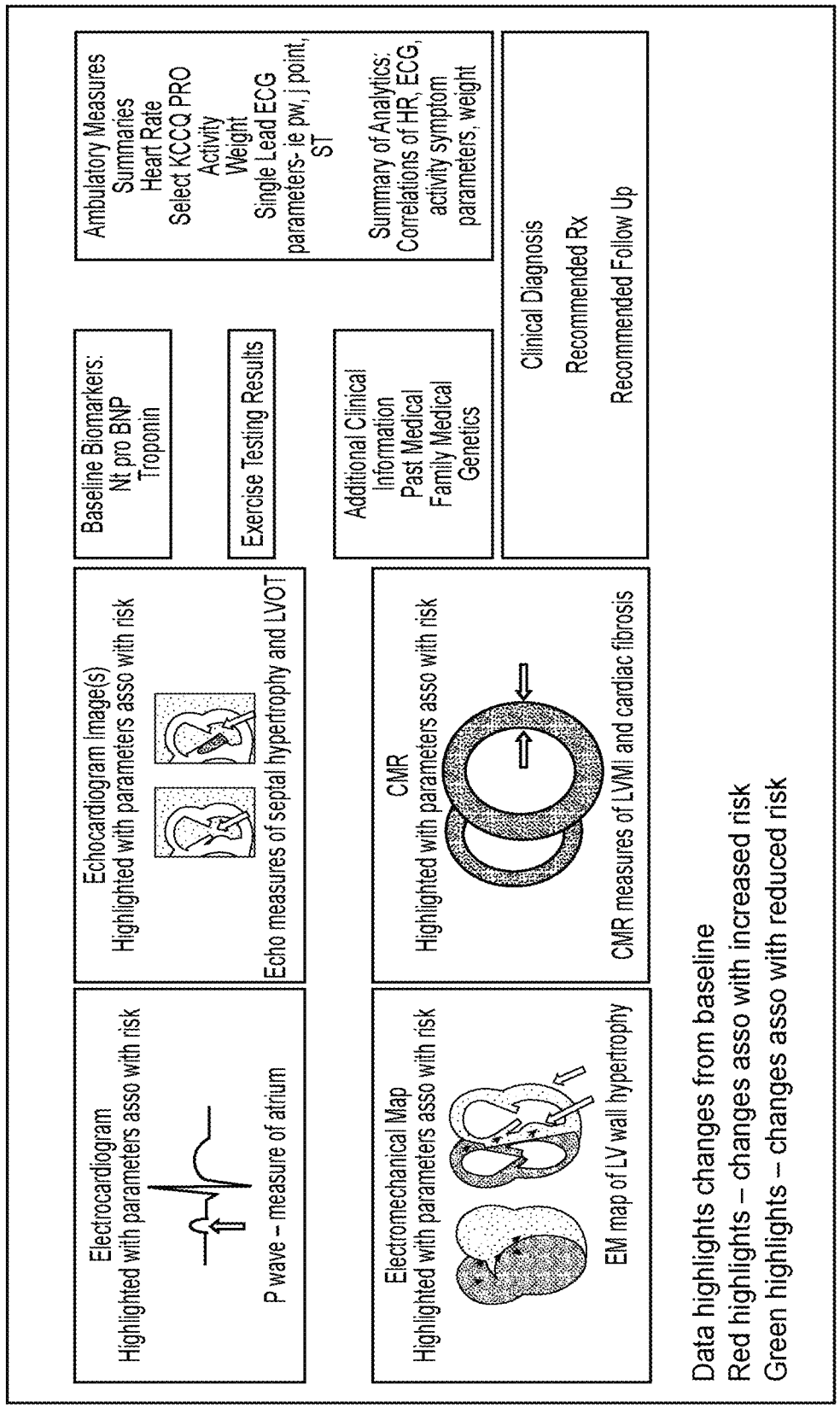
FIG. 9B depicts an exemplary illustration of a cardiac health status determination subsequent to the baseline evaluation, in accordance with an embodiment.
Figure 16:
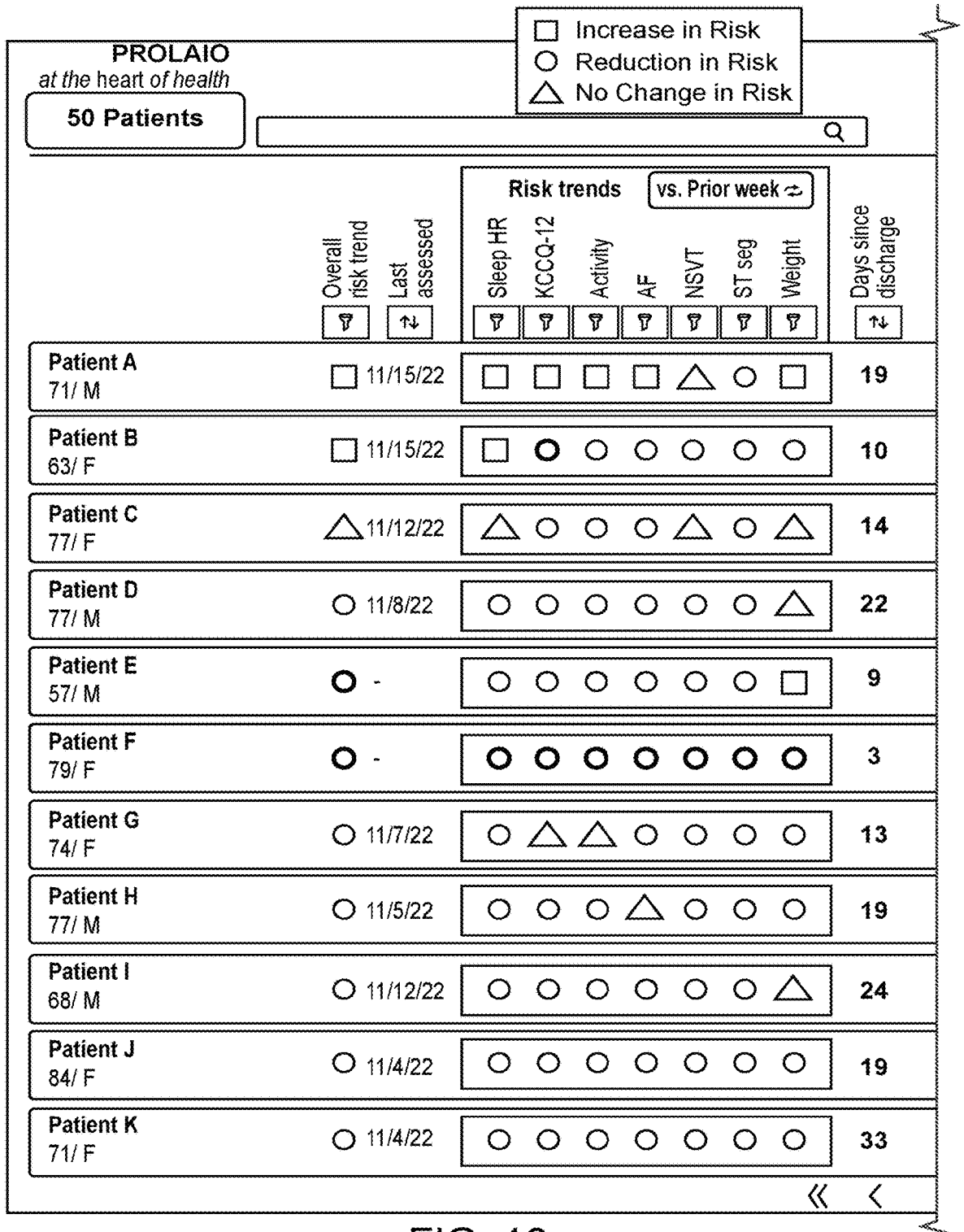
Figure 17:
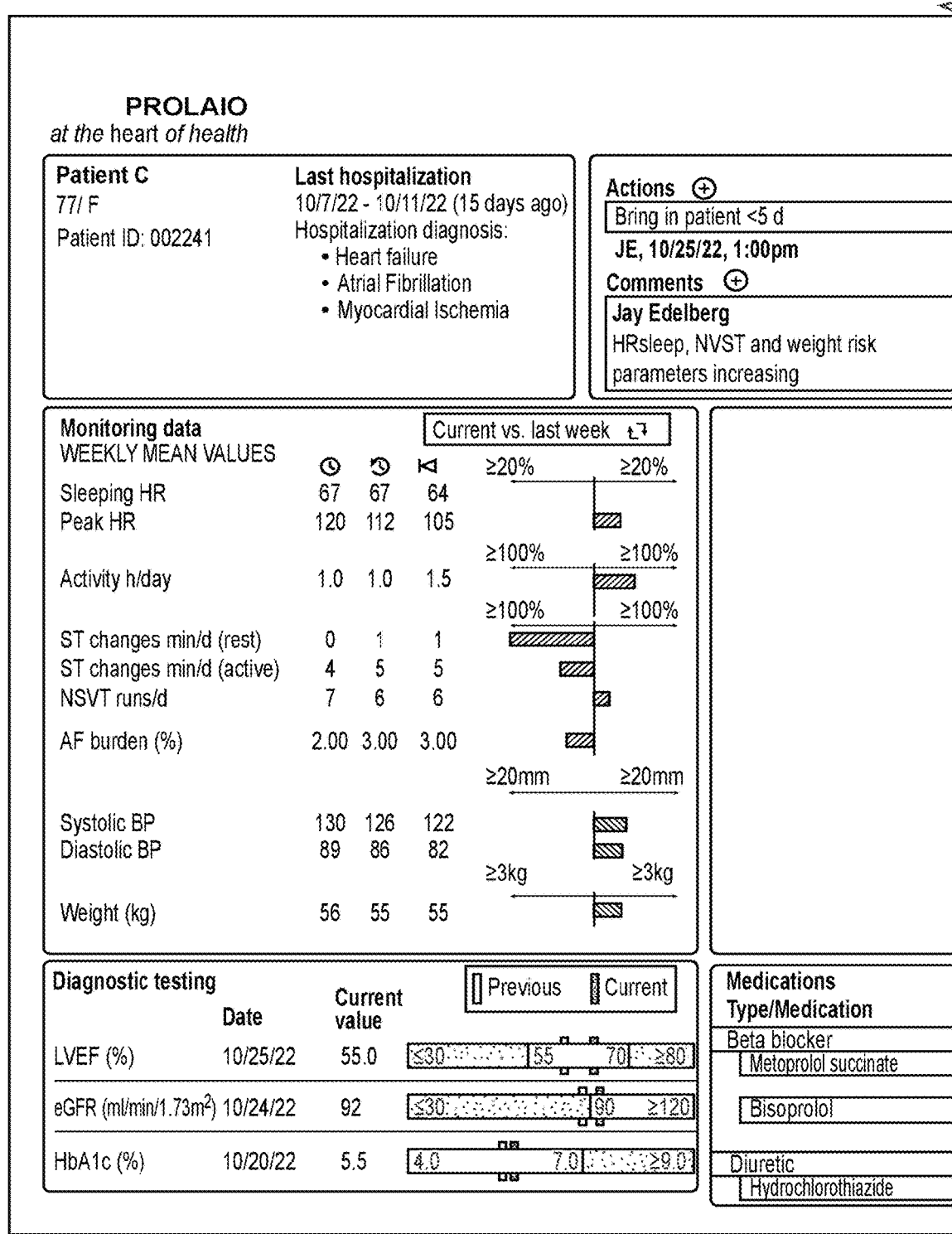
Figure 17:
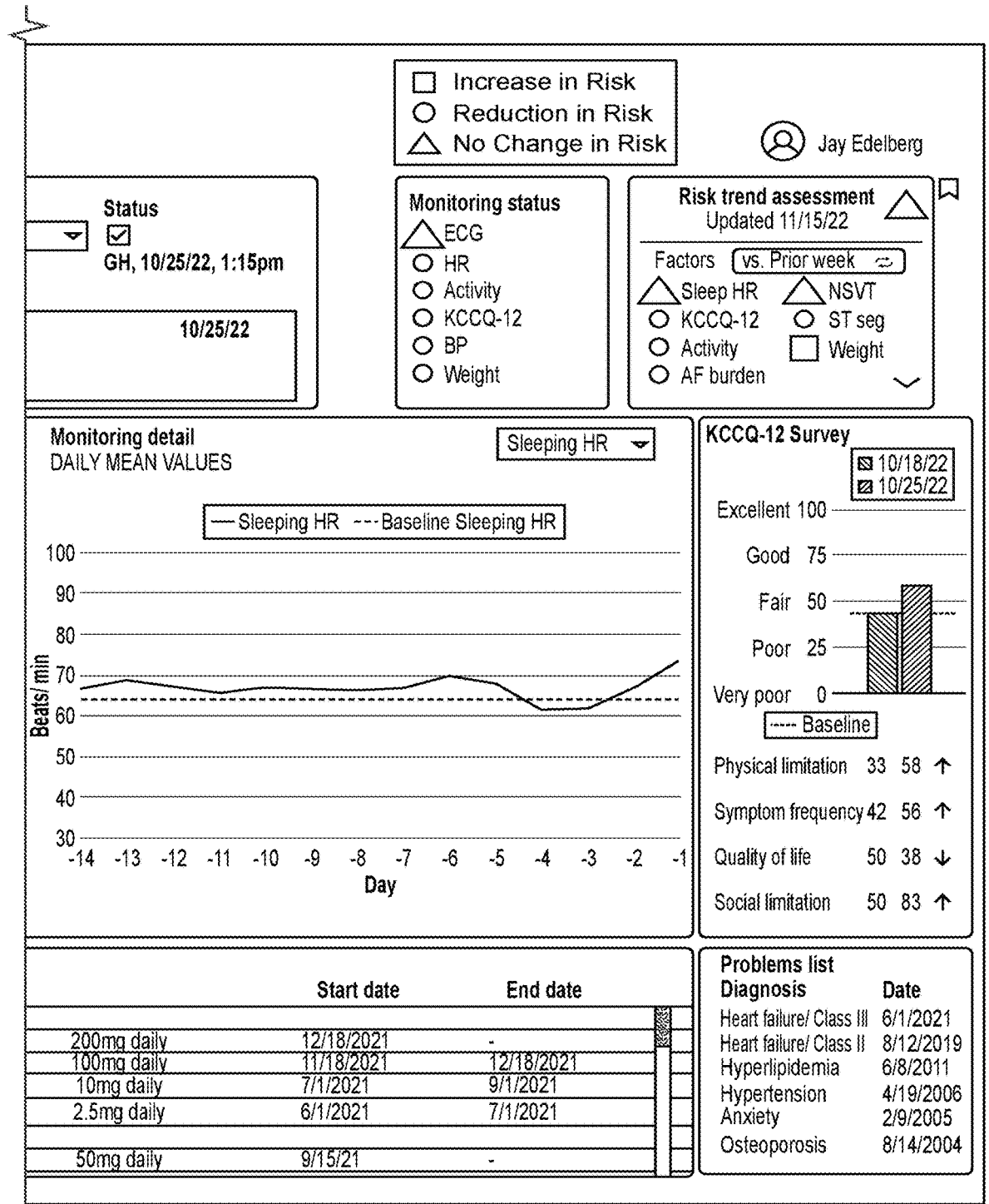
Figure 18:
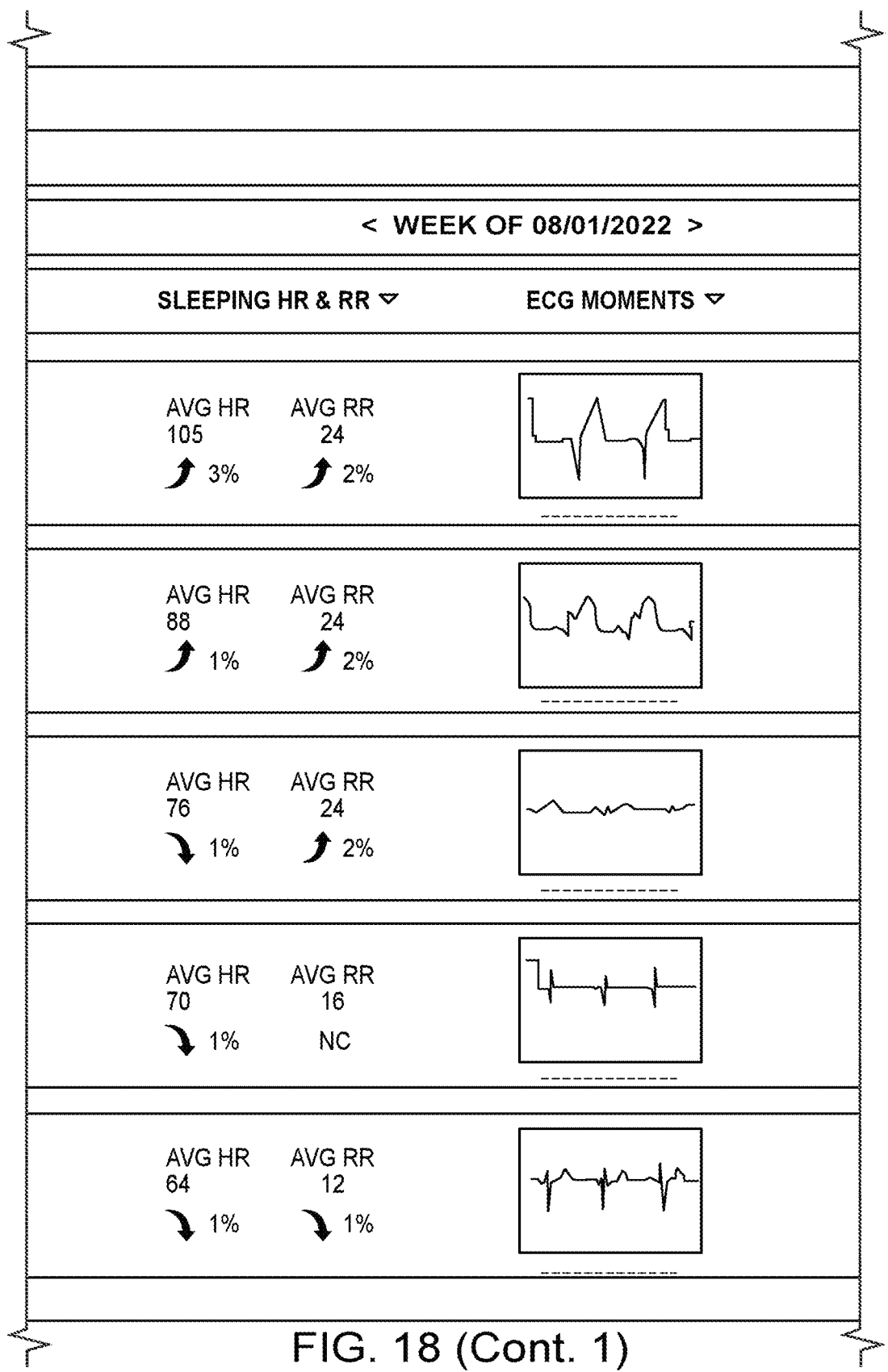

FIG. 9B depicts an exemplary illustration of a subsequent cardiac health status evaluation, which highlights the changes from the baseline evaluation. For example, in some cases, the changes are highlighted in a color, where a first color may be associated with an increased risk (of developing a cardiac condition) or detection of a new cardiac condition, while a second color may be associated with a reduced risk (of developing a cardiac condition). For example, FIG. 16 provides an exemplary output of parameters monitored for a plurality of subjects, wherein a risk trend of certain parameters are compared from a prior week. As depicted in FIG. 16, a square correlates for an increased risk based on a change of the given parameter (an increased risk may also be identified by color, e.g., red), a circle correlates with a reduced risk (which may be identified by color, e.g., green), and a triangle correlates no change to a risk (which may be identified by color, e.g., yellow).

In some embodiments, periodic monitoring by the MM module 212 enables for reduced the risk of the subject developing a cardiac condition, and/or in some cases, help prevent such cardiac condition entirely. For example, in some cases, heart failure with preserved ejection fraction (HFpEF), a clinical syndrome associated with a high morbidity and mortality, has an increased risk of developing in a subject with atrial fibrillation. As described herein, the DRP module 210 is configured to detect not only the risk of detecting atrial fibrillation, but also the risk of developing atrial fibrillation. Accordingly, for subjects identified with a risk of developing atrial fibrillation, the system 100 is configured to help in directing therapies to help reduce and prevent atrial fibrillation, and thereby reducing the onset of HFpEF.

Figure 10:
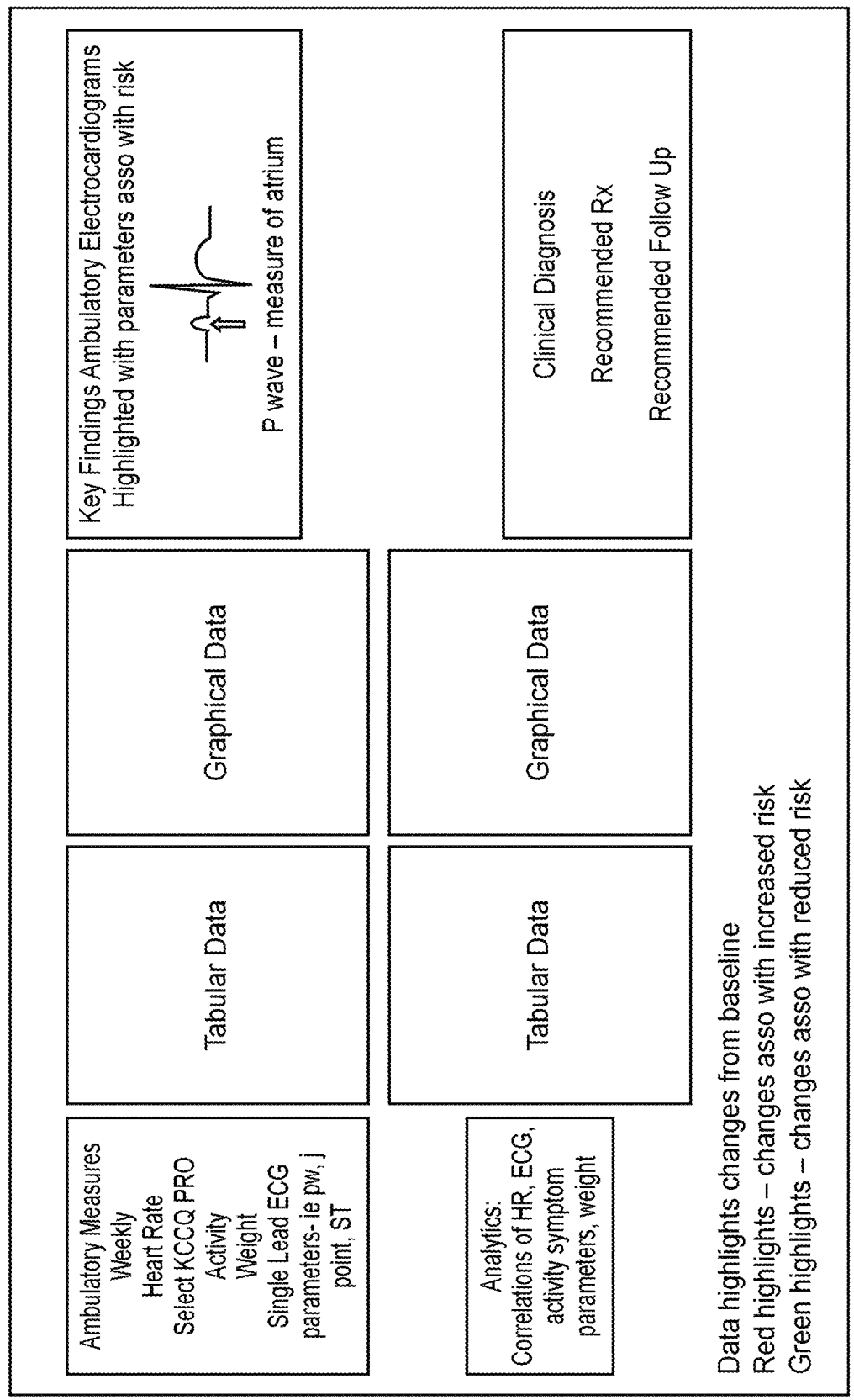
FIG. 10 depicts an exemplary illustration of an ambulatory monitoring output, in accordance with an embodiment.

In some embodiments, periodic ambulatory monitoring by the MM module 212, including of health parameters such as weight, activity, and cardiac biomarkers, provides a more targeted monitoring of the cardiac health status and helps reducing the risk for an adverse outcome (e.g., developing a cardiac condition such as stroke, sudden death, atrial fibrillation, etc.). FIG. 10 depicts an exemplary illustration of an output by the system 100 relating to ambulatory monitoring.

Intervention Recommendations

In some embodiments, the intervention module 214 is configured to recommend a therapy and/or treatment as intervention method for a detected cardiac condition and/or risk of a cardiac condition in a subject. In some embodiments, the intervention module 214 is also configured to receive a recommendation for therapy by a healthcare professional.

In some embodiments, the intervention module 214 is further configured to evaluate the efficacy of a therapy undertaken by the subject. For example, in some embodiments, the intervention module 214 identifies a therapy currently being undertaken by the subject, correlating the therapy with one or more targeted cardiac conditions. The intervention module 214 is then configured to identify the changes to the relevant health parameters, cardiac condition detection, and/or cardiac condition risk (e.g., risk score) via the MM module 212 (see for example FIG. 9B), wherein the intervention module 214 correlates the changes with an increased or reduced risk of the cardiac condition targeted by the therapy. In some embodiments, wherein the risk of the cardiac condition increased, the intervention module is configured to recommend a new therapy and/or alert the subject and/or a healthcare provider to stop continuing with the therapy. In some embodiments, the intervention module 214 is configured to access the one or more decision engines to identify the relevant health parameters associated with the cardiac condition, so as to correlate changes with an increase or reduced risk of the cardiac condition.

In some embodiments, the intervention module 214 is configured to aid in the development of new therapies/treatments by providing continuous monitoring of one or more health parameters (e.g., ECG parameters), and thereby enabling effective management of a therapy. In some cases, such monitoring (e.g., ambulatory monitoring), will reduce the need for in person clinics or other imaging (such echocardiography) so as to evaluate the efficacy of a treatment.

In an exemplary embodiments, the system 100, via the intervention module 214, is configured to evaluate and assess the use of myosin inhibition therapy for hypertrophic cardiomyopathy (HCM). In some embodiments, one or more decision engines are configured to correlate with, and potentially predict, the HCM benefits and risk (for e.g., systolic dysfunction) of myosin inhibition therapy in clinical practice. For example, in some embodiments, baseline and treatment related changes in health parameters (e.g., ECG parameters) that correlate myosin inhibitor benefits and risk will be analyzed. In some embodiments, the one or more decision engines will be combined with additional ECG elements generated with supervised and unsupervised strategies. For example, supervised testing may include a focus on potential changes related to left ventricular loading conditions (p waves changes associated with left atrial enlargement), measures of atrial fibrillation risk, and QRS changes linked to pulmonary hypertension. In addition, the one or more decision engines may include other measures of risk including NT proBNP, troponin, left ventricular mass as well as ejection fraction to be incorporated in the correlations of clinical risk.

Communication

In some embodiments, the communication module 216 is configured to communicate with a healthcare provider, to send alerts and/or cardiac health statuses, and/or relay to the subject or the cardiac health tool 106 (and associated modules) recommendations, data (such as additional health parameters, including clinical biomarkers and/or images), and messages to the subject.

In some embodiments, as described herein, the cardiac health tool 106 is configured to display the subject's health parameters and/or cardiac health status using a display interface (e.g., a monitor, screen, etc.).

III. Methods for Determining a Cardiac Health Status

Figure 3:
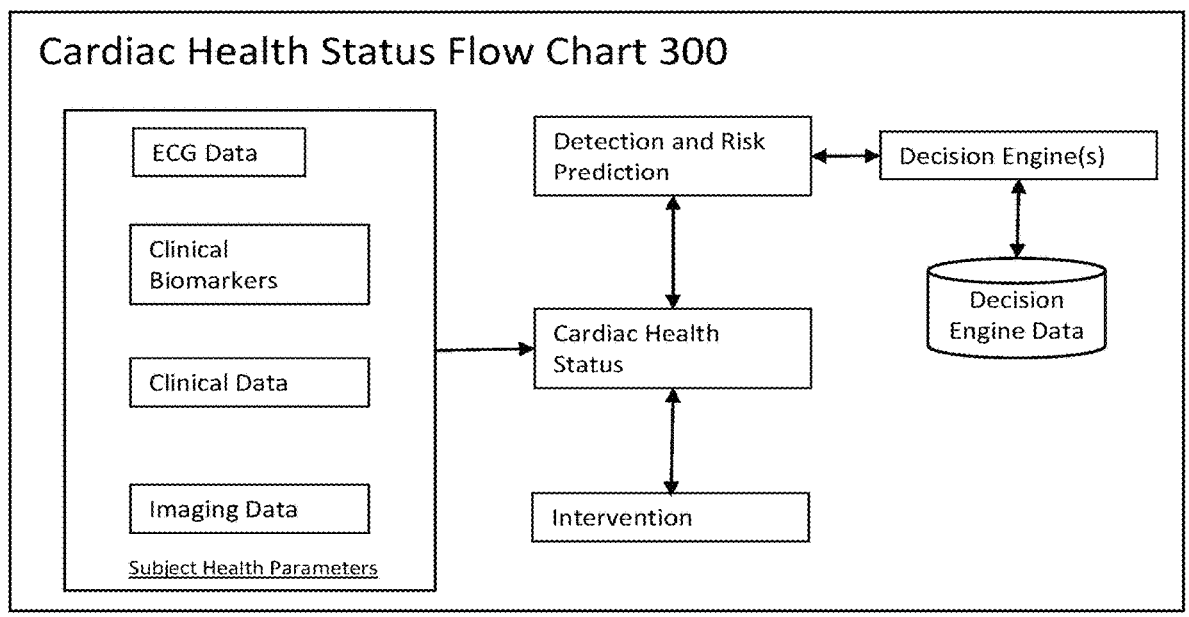
FIG. 3 depicts an exemplary flow chart for determining a cardiac health status, in accordance with an embodiment.

Embodiments described herein include methods for determining a cardiac health status for a subject by applying one or more decision engines to the subject's health parameters, which may include ECG data. Such methods can be performed by the cardiac health tool described in FIG. 2A. FIG. 3 depicts an example flow diagram 300 for determining a cardiac health status, in accordance with an embodiment. As shown in FIG. 3, the cardiac health status is determined based on input through one or more subject health parameters, wherein cardiac condition is detected and/or a risk of a cardiac condition is predicted using one or more decision engines. In some embodiments, an intervention (e.g., therapy/treatment) is recommended and/or evaluated for efficacy. As described herein, the subject health parameters can include ECG data (including specific ECG parameters as described herein), clinical biomarkers, clinical data (as described herein), and/or imaging data. In some embodiments, the different types of subject health parameters are updated at different frequencies. For example, in some embodiments, the ECG data and other health parameters (such as weight, heart rate, BMI) can be retrieved hourly, every 12 hours, daily, every other day, weekly, etc., via a device, such as a wearable device. In some embodiments, health parameters such as clinical biomarkers are obtained by the clinical biomarker module less frequently than, for example ECG data. For example, in some embodiments, clinical biomarkers are obtained from about daily to about semi-annually, such as weekly, bi-weekly, monthly, bi-monthly, etc. As described herein, for a given cardiac condition, the cardiac health status tool applies one or more corresponding decision engines using a prescribed permutation of health parameters. For example, in some embodiments, in determining a particular cardiac condition, a prescribed set of ECG parameters of the ECG data obtained will only be used. Accordingly, in some embodiments, the DRP module 210, via communication with the corresponding one or more decision engines, will extract the required ECG parameters via the ECG data module 200 (similar for other health parameters for other modules).

Figure 5:
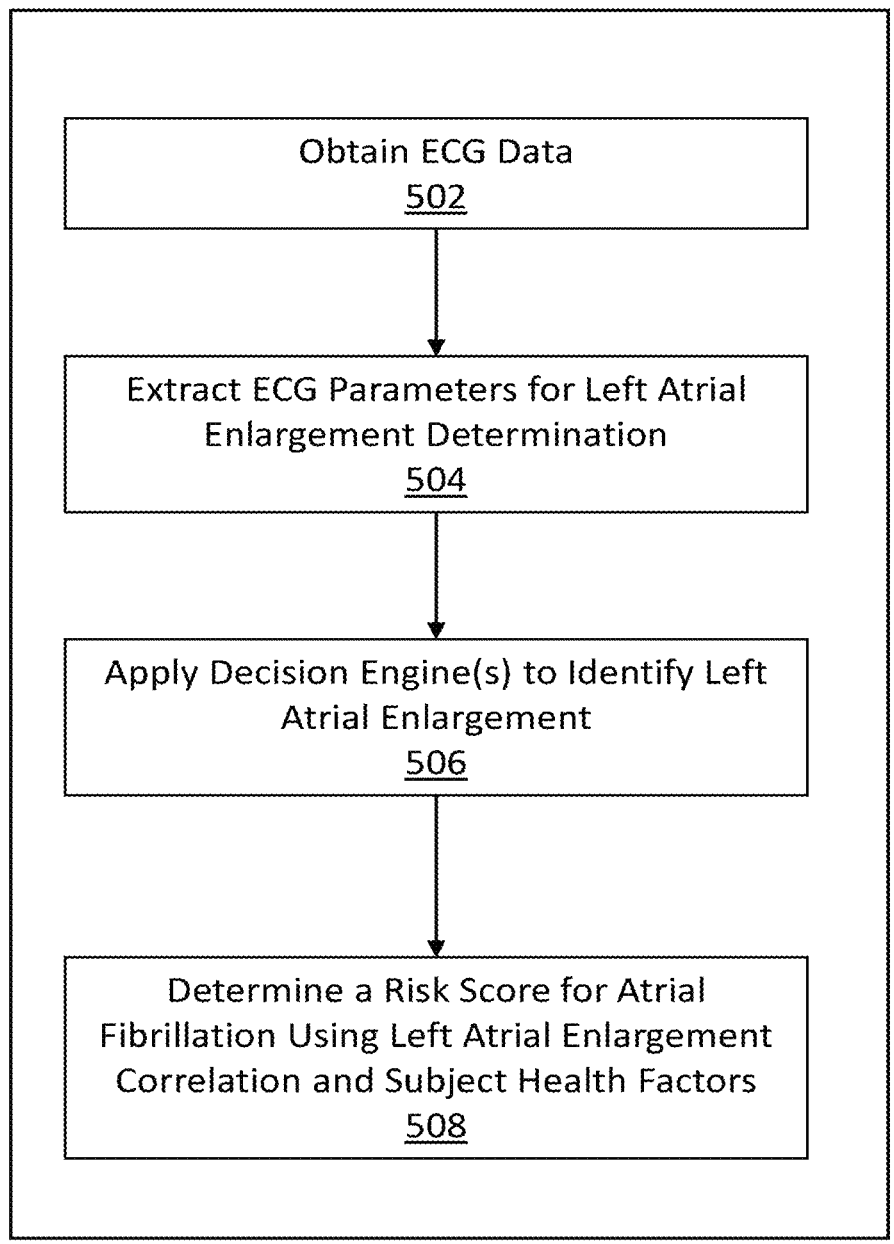
FIG. 5 depicts an exemplary flow chart for a method for determining a risk score for atrial fibrillation, in accordance with an embodiment.

FIG. 5 provides an exemplary process flow for predicting a risk score for developing atrial fibrillation in a subject using an embodiment of the system described herein. In some embodiments, the system first obtain ECG data 502 (for example, via the ECG data module 200 as described herein). The ECG data module 200 may then extract specific ECG parameters 504 from the ECG data, via communication with a decision engine. The DRP module 210 may then apply a decision engine to correlate the ECG parameters with left atrial enlargement 506. The DRP module may then determine a risk score 506 based on the left atrial enlargement and one or more other health factors. In some embodiments, the risk score is outputted (for e.g., to a display as described herein) as part of the cardiac health status.

Figure 6:
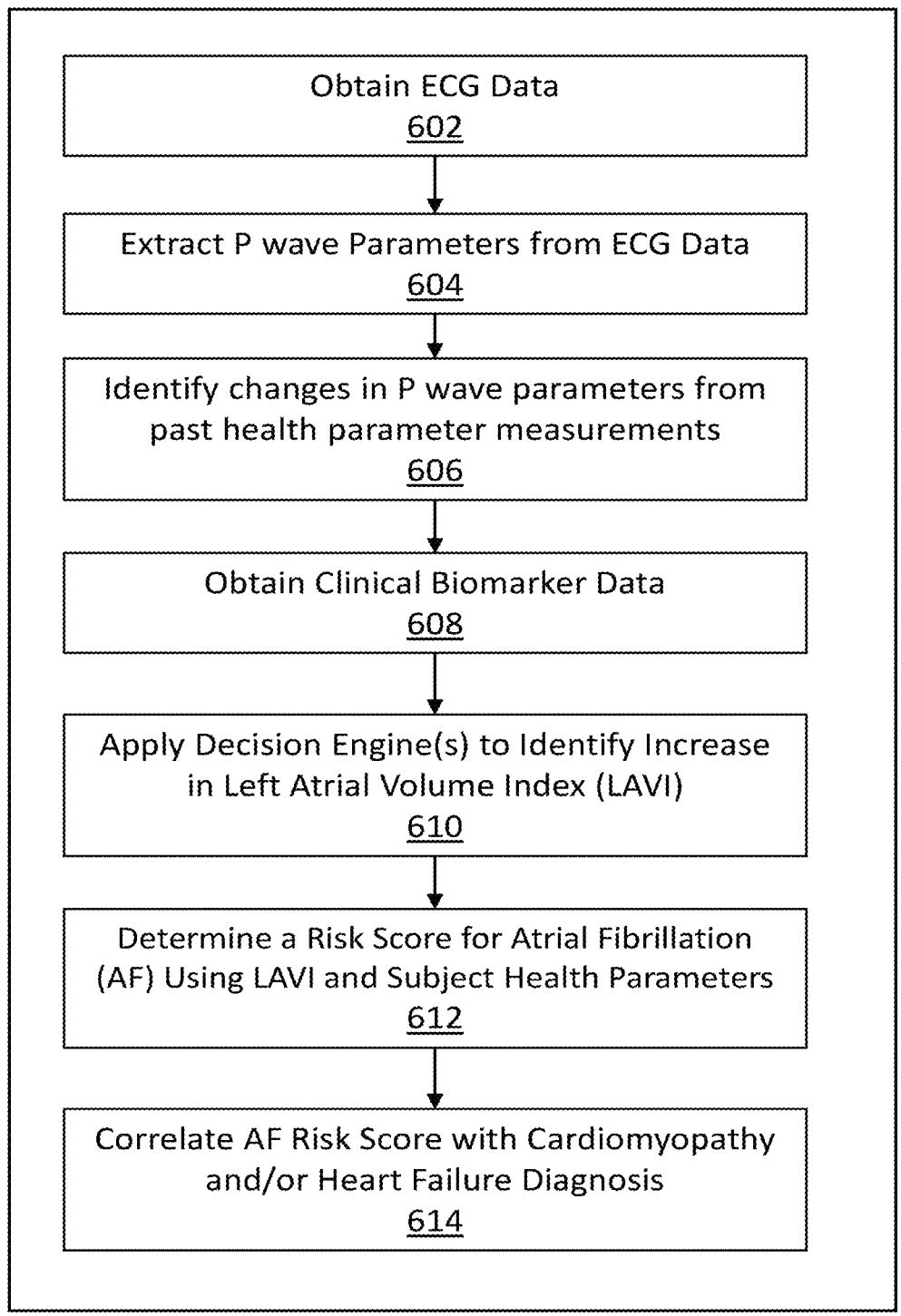
FIG. 6 depicts an exemplary flow chart for a method for determining a risk score for atrial fibrillation and detection for cardiomyopathy and/or heart failure, in accordance with an embodiment.

FIG. 6 provides an exemplary process flow for predicting a risk score for developing atrial fibrillation in a subject along with detection of cardiomyopathy and/or heart failure, using an embodiment of the system described herein. In some embodiments, the system first obtain ECG data 602 (for example, via the ECG data module 200 as described herein). The ECG data module 200 may then extract specific ECG parameters 604 from the ECG data, via communication with a decision engine. For example, the ECG data module 200 may extract P wave parameters from the ECG data. The MM module 212 may identify changes to P wave parameters 606 from past health parameter measurements. The system 100 may then obtain clinical biomarker data 608, which may have already been stored in the clinical biomarker module 202. An exemplary clinical biomarker is NT-proBNP. In some cases, changes to clinical biomarkers (as identified by the MM module 212) may be identified. The DRP module 210 may then apply a decision engine 610 to correlate the change in ECG parameters (e.g., change in P wave parameters) and clinical biomarkers (e.g., NT-proBNP) (which may or may not be based on changes) with an increase in the left atrial volume index (LAVI). The DRP module may then determine a risk score 612 based on the LAVI and one or more other health parameters. The DRP module 210 may then correlate the risk score of atrial fibrillation, along with one or more other health parameters (including, in some cases, reported symptoms), to detect cardiomyopathy and/or heart failure, and optionally identify a respective severity. In some embodiments, the risk score and cardiac condition detection is outputted (for e.g., to a display as described herein) as part of the cardiac health status.

Figure 7:
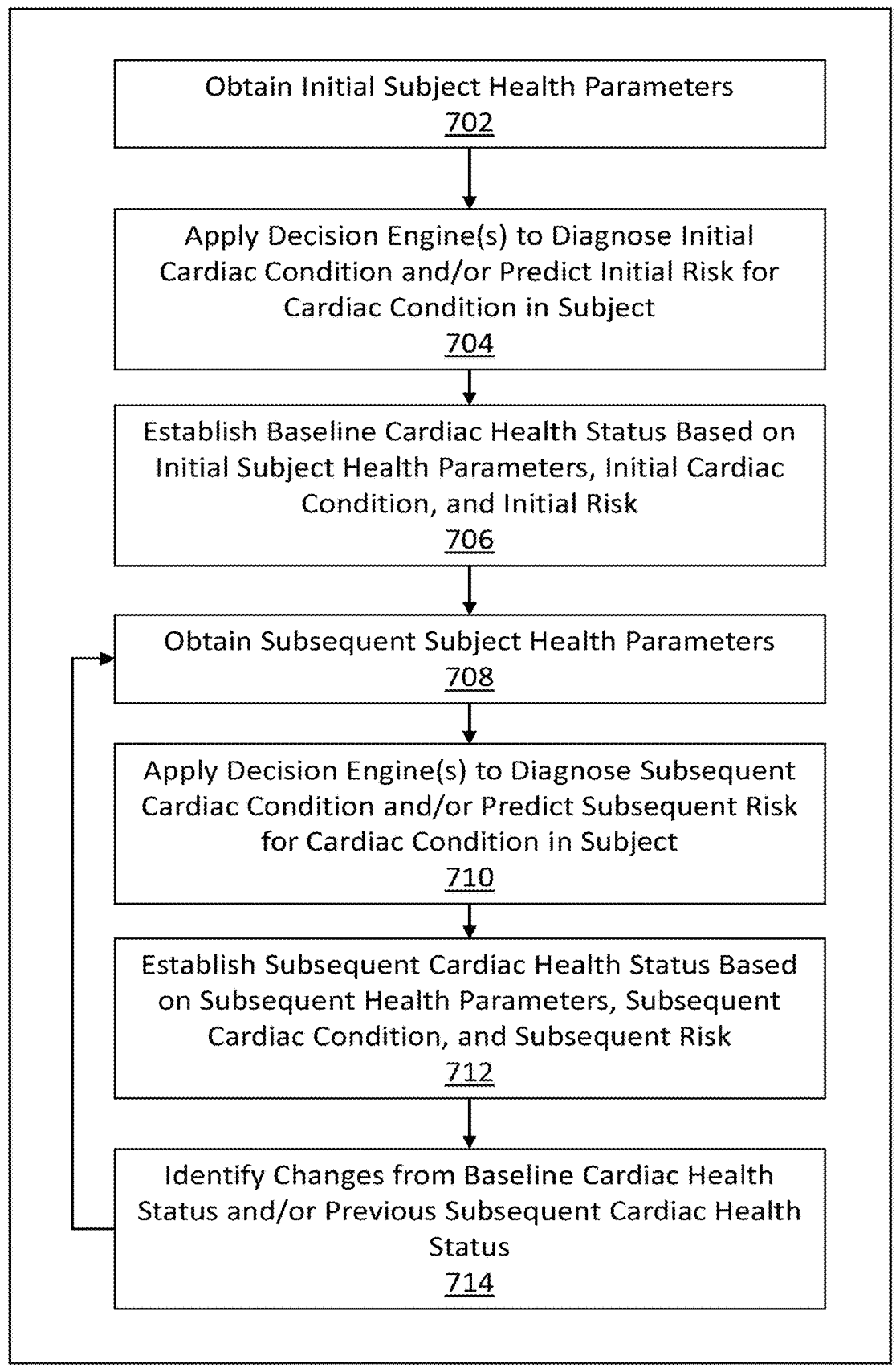
FIG. 7 depicts an exemplary flow chart for a method for monitoring a cardiac health status of a subject, in accordance with an embodiment.

FIG. 7 provides an exemplary process flow for monitoring a cardiac health status, according to an embodiment described herein. In some embodiments, the system first obtains health parameters (e.g., ECG data, clinical data, etc.) 702 correlating to an initial measurement/input. In some embodiments, one or more health parameters are obtained via ambulatory measurement (ambulatory monitoring parameters). In some embodiments, one or more health parameters are obtained from a hospital or medical location (e.g., a clinic). The term "subject health parameters" or "subject health factors" may be used interchangeably herein. The DRP module may then apply one or more decision engines 704 to diagnose a cardiac condition in the subject and/or predict a risk for a cardiac condition in the subject, thereby providing an initial diagnosis and prediction. The MM module 212 may then establish a baseline cardiac health status 706 for the subject, based on the initial health parameters and cardiac condition detection and/or risk prediction. The MM module 212 may then retrieve a subsequent measurement of health parameters (e.g., via an ECG device and/or other ambulatory monitoring) 708. The DRP module 210 may then apply the decision engine(s) again to determine if there is a change to the cardiac condition(s) detected and/or risk score predictions 710. The MM module 212 may then establish a subsequent cardiac health status 712, and further identify the changes from the baseline evaluation 714. The MM module 212 may then retrieve a subsequent measurement of health parameters again (e.g., via ambulatory monitoring), restarting the steps at 708, wherein at step 714, the MM module 212 may identify changes from the baseline evaluation and also from the previous cardiac health status. Steps 708 to 714 may be repeated according to a periodic frequency, such as hourly, daily, weekly, monthly, etc. In some embodiments, the system is further configured to output the change in cardiac health status, and/or to alert the subject and/or a medical professional of said change. In some embodiments, the DRP module 210 does not require the same health parameters in order to establish a cardiac health status. For example, in some cases, certain measurements are not performed according to the same periodic frequency (e.g., blood pressure), wherein the DRP module is configured to account for such absent data to establish the cardiac health status.

Figure 8:
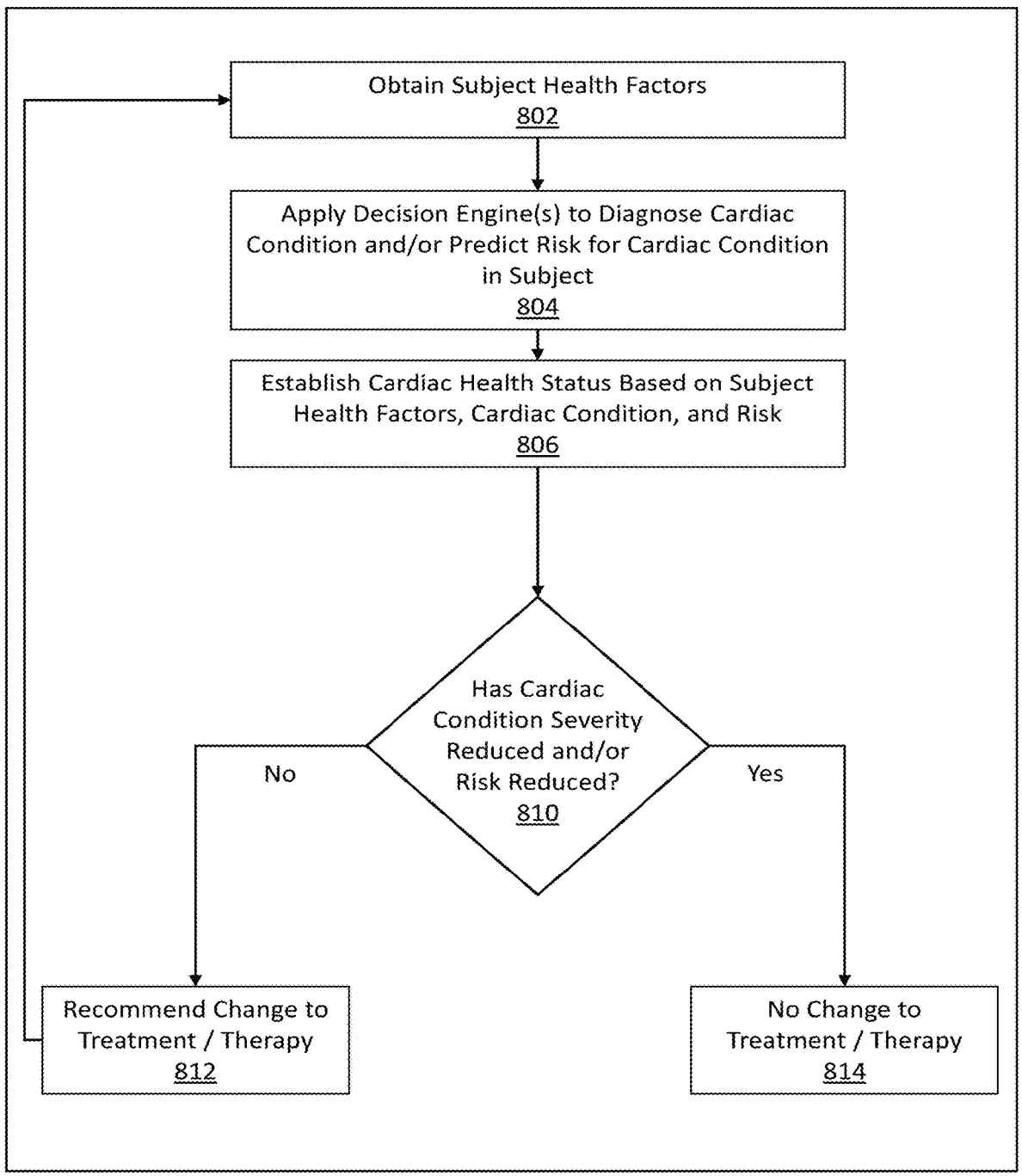
FIG. 8 depicts an exemplary flow rate for a method for evaluating an efficacy of a therapy, in accordance with an embodiment.

FIG. 8 provides an exemplary flow process for evaluating the efficacy of a therapy/treatment undertaken by the subject with regards to a cardiac condition and/or cardiac condition risk. In some embodiments, the intervention module 214 identifies the therapy undertaken by the subject and correlates identifiers (e.g., health parameters and/or cardiac condition parameters) to determine the efficacy of the therapy. Alternatively and/or in combination, the intervention module 214 may seek to identify only a change in status of one or more parameters, risk scores, or cardiac condition detections to identify an efficacy of a therapy. The MM module 212 may first retrieve health factors (e.g., ECG data) 802. In some embodiments, the health factors are obtained via ambulatory monitoring. The DRP module may then apply one or more decision engines 804 to detect a cardiac condition and/or a risk score for a cardiac condition. The MM module 212 may then establish a cardiac health status 806 (as described herein). The intervention module 214 may then determine whether a severity in a cardiac condition has reduced and/or a risk score for a cardiac condition has reduced 810. If a reduction is observed, then the intervention module 214 may not recommend any changes to the therapy. In some embodiments, a reduction being observed in correlation with the therapy indicates that the therapy is a high efficacy therapy. If no reduction is observed, then the intervention module may recommend a change to the treatment/therapy 812. In some cases, once a new therapy/treatment is undertaken by the subject, steps 802 to 814 will be repeated to once again determine the efficacy of the therapy. In some embodiments, the system is configured to identify and propose a new therapy based on the respective cardiac condition and subject health factors of the subject.

Figure 12:
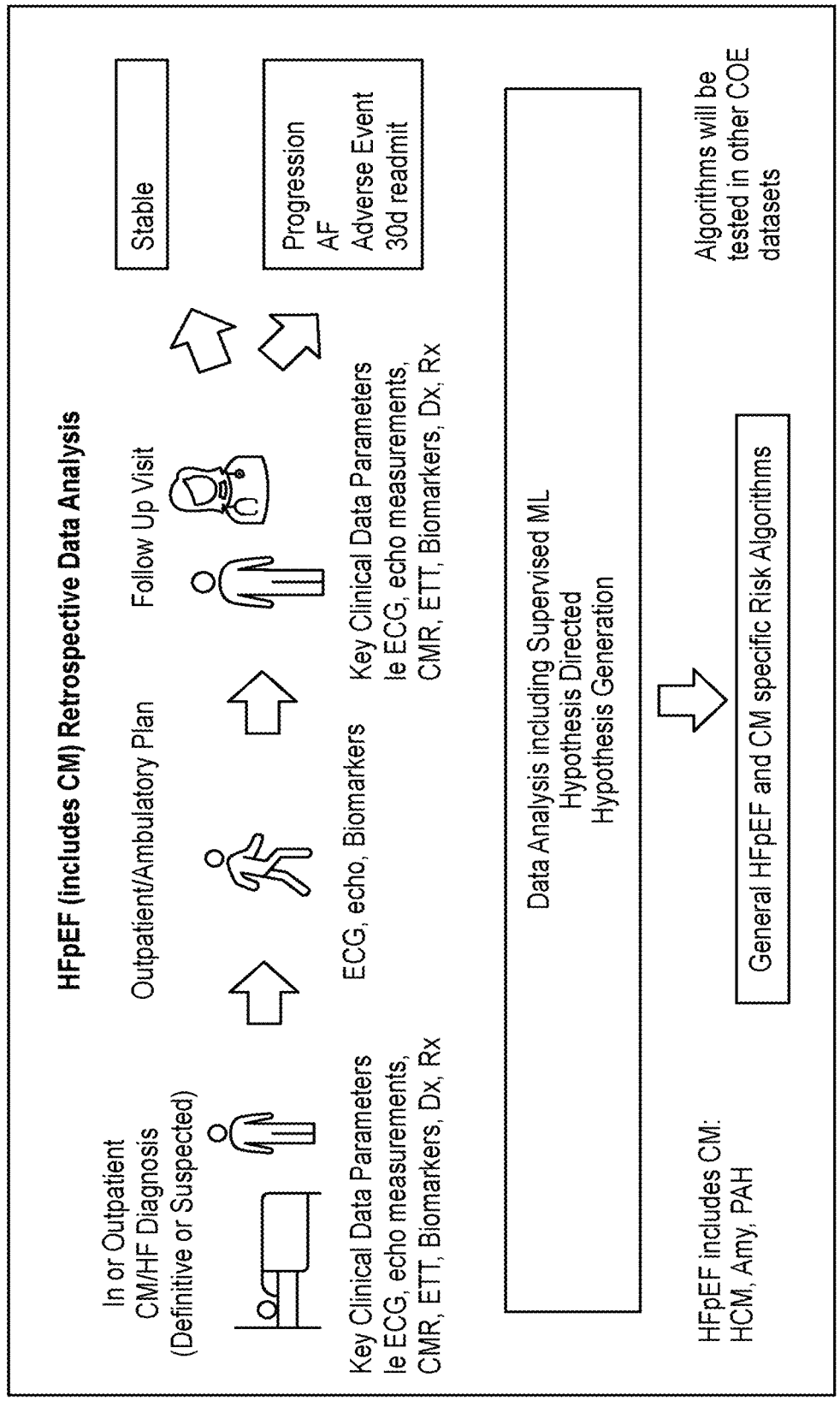
FIG. 12 depicts an exemplary illustration of a process relating to heart failure with preserved ejection fraction (HFpEF) without determining a cardiac health status, in accordance with an embodiment.
Figure 13:
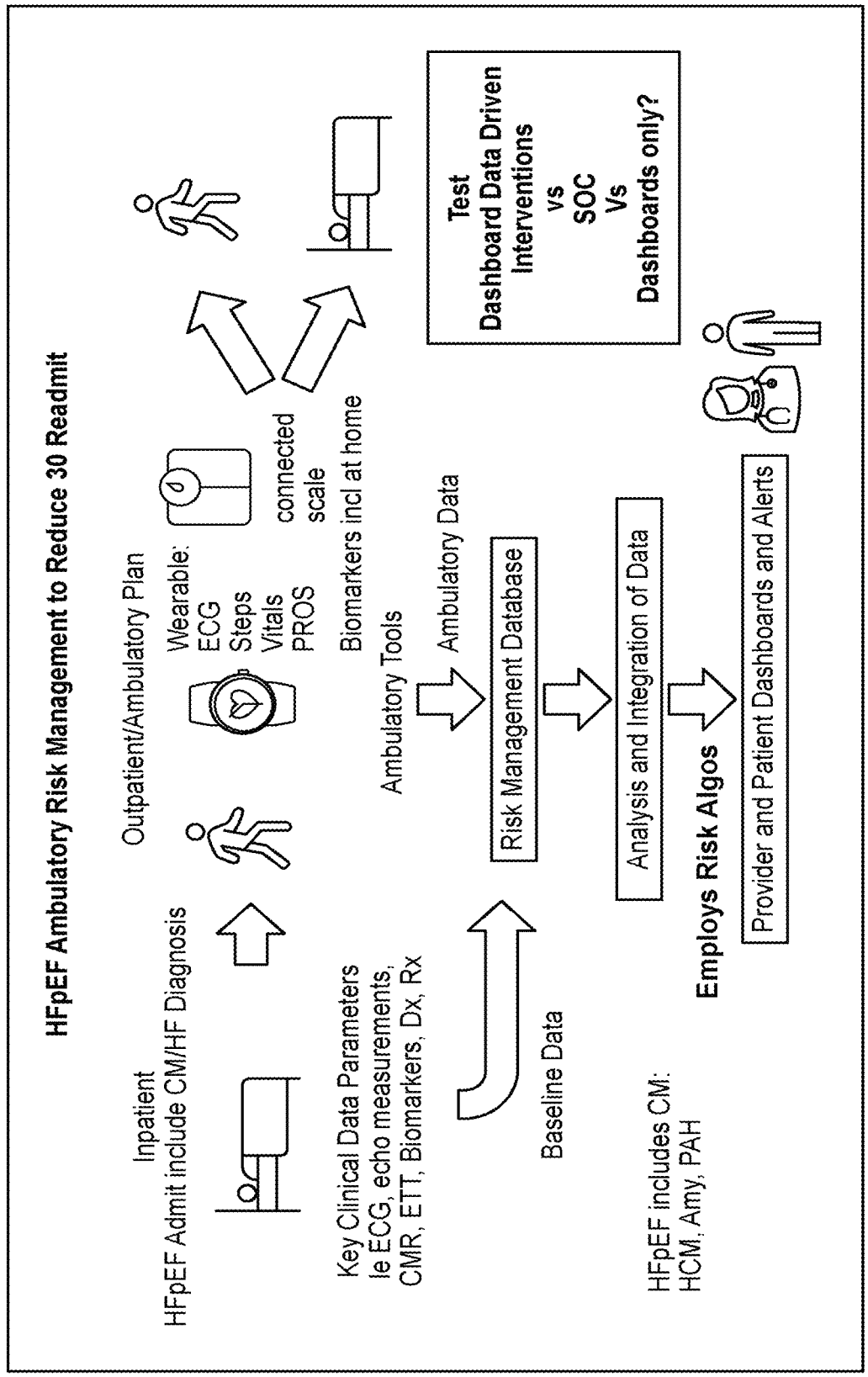
FIG. 13 depicts an exemplary illustration of a process relating to heart failure with preserved ejection fraction (HFpEF) with determining a cardiac health status, in accordance with an embodiment.

FIGS. 12 and 13 provide an exemplary illustration of the above-described techniques for monitoring a cardiac health status with specific reference to HFpEF and helping reduce the number of 30 day readmission rates. For example, FIG. 12 depicts using certain ambulatory data to be reviewed with a follow-up visit with a medical professional, so as to identify the status of the subject's cardiac health and any potential progression of cardiac conditions. FIG. 13 depicts using the system to generate a baseline cardiac health status, with subsequent ambulatory monitoring of the subject (e.g., via ECG data, weight, etc.) allowing the system to monitor and identify changes in cardiac health status, which can be communicated to a medical health professional. For example, if the subsequent monitoring of the subject's cardiac health status identifies an increased risk of developing a cardiac condition, including potentially leading to a readmission to a hospital and/or medical location, the medical professional can be alerted and allowed to provide a recommendation. Accordingly, such cardiac health status monitoring can be obtained more frequently and readily, further reducing time loss otherwise associated with having the subject to travel to a hospital or other medical location for such monitoring.

IV. Computer Implementation

The methods described herein, including the methods of implementing one or more decision engines for determining a cardiac health status, are, in some embodiments, performed on one or more computers.

For example, the building and deployment of any method described herein can be implemented in hardware or software, or a combination of both. In one embodiment, a machine-readable storage medium is provided, the medium comprising a data storage material encoded with machine readable data which, when using a machine programmed with instructions for using said data, is capable of executing any one of the methods described herein and/or displaying any of the datasets or results (e.g., cardiac condition detection, risk prediction) described herein. Some embodiments can be implemented in computer programs executing on programmable computers, comprising a processor and a data storage system (including volatile and non-volatile memory and/or storage elements), and optionally including a graphics adapter, a pointing device, a network adapter, at least one input device, and/or at least one output device. A display may be coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high-level procedural or object-oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of an embodiment. The databases of some embodiments can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

In some embodiments, the methods described herein, including the methods for determining a cardiac health status, are performed on one or more computers in a distributed computing system environment (e.g., in a cloud computing environment). In this description, "cloud computing" is defined as a model for enabling on-demand network access to a shared set of configurable computing resources. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

FIG. 4 illustrates an example computer for implementing the entities shown in FIGS. 1-3, and 5-11B. The computer 400 includes at least one processor 402 coupled to a chipset 404. The chipset 404 includes a memory controller hub 420 and an input/output (I/O) controller hub 422. A memory 406 and a graphics adapter 412 are coupled to the memory controller hub 420, and a display 418 is coupled to the graphics adapter 412. A storage device 408, an input device 414, and network adapter 416 are coupled to the I/O controller hub 422. Other embodiments of the computer 400 have different architectures.

The storage device 408 is a non-transitory computer-readable storage medium such as a hard drive, compact disk read-only memory (CD-ROM), DVD, or a solid-state memory device. The memory 406 holds instructions and data used by the processor 402. The input interface 414 is a touch-screen interface, a mouse, track ball, or other type of pointing device, a keyboard, or some combination thereof, and is used to input data into the computer 400. In some embodiments, the computer 400 may be configured to receive input (e.g., commands) from the input interface 414 via gestures from the user. The network adapter 416 couples the computer 400 to one or more computer networks.

The graphics adapter 412 displays images and other information on the display 418. In various embodiments, the display 418 is configured such that the user may (e.g., subject, healthcare professional, non-healthcare professional) may input user selections on the display 418 to, for example, initiate the system for determining a cardiac health status. In one embodiment, the display 418 may include a touch interface. In various embodiments, the display 418 can show a cardiac health status for the subject and associated monitoring. Thus, a user who accesses the display 418 can inform the subject of the cardiac health status. In various embodiments, the display 418 can show information such as depicted in FIGS. 9A-11B.

The computer 400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 408, loaded into the memory 406, and executed by the processor 402.

The types of computers 400 used by the entities of FIGS. 1-3 can vary depending upon the embodiment and the processing power required by the entity. For example, the cardiac health tool 106 can run in a single computer 400 or multiple computers 400 communicating with each other through a network such as in a server farm. The computers 400 can lack some of the components described above, such as graphics adapters 412, and displays 418.

V. Systems

Further disclosed herein are systems for implementing one or more decision engines for detecting a cardiac condition and/or predicting a risk for a cardiac condition. In various embodiments, such a system can include at least the cardiac health tool 106 described above in FIG. 1. In some embodiments, the cardiac health tool 106 is embodied as a computer system, such as a computer system with example computer 400 described in FIG. 4.

In some embodiments, the system includes one or more auxiliary devices, such as an ECG device, an ambulatory monitoring device, an imaging device, an accelerometer, a weight scale, etc., or any combination thereof, as described herein. In some embodiments, the system includes both the cardiac health tool 106 (e.g., a computer system) and one or more of the auxiliary devices. In such embodiments, the cardiac health tool 106 can be communicatively coupled with any combination of the auxiliary devices to receive data therefrom.

VI. Examples

Example 1: Detection of Changes in High Risk Parameters

Figure 19:
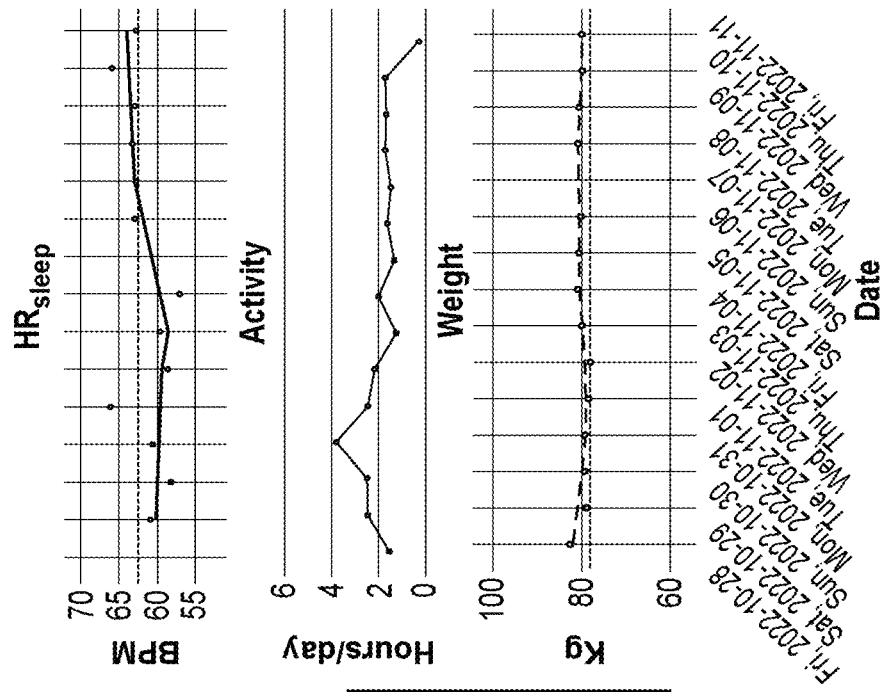
FIG. 19 depicts an exemplary summary of clinical parameter monitoring for a patient over a two-week period.

Disclosed in FIG. 19 includes a summary of certain clinical parameters monitored for a subject over two weekly periods (Week 1 and Week 2), according to a system and method described herein. The subject was a 39 year old female, whose relevant health history included a mitral valve prolapse in 2019, having COVID-19 three times, and suffering from heartburn in 2018. The subject was also taking pepcid, loratadine, inositol, and choline as medication at the time of the monitoring. The subject further was suffering from an allergic skin reaction to an ECG patch, and was having flu like symptoms (as noted under the "Reported Adverse Events" (AE)).

As depicted, the system monitored and detected a change from Week 1 to Week 2 in i) heart rate when asleep, ii) daily activity by the subject, and iii) weight. Specifically, the subject was identified as having an increase in heart rate (while asleep) by 5.0 bpm, wherein the mean change in heart rate for six other healthy individuals was −1.7, a decrease in activity of 0.7 hours, and a weight gain of 0.9 kg. The graphs on the right side of FIG. 19 depict the daily trend of heart rate (when asleep), activity, and weight from Oct. 28, 2022 to Nov. 11, 2022.

The subject then visited her cardiologist on Nov. 11, 2022, where follow-up testing was requested by the cardiologist, which revealed that the increase in heart rate while asleep and reduced daily activity were associated with an increase in the incidence of tachyarrhythmia.

Accordingly, the system, was able to identify that changes in high risk parameters, such as increase in heart rate while asleep and reduction in activity, correlated with an increase in health risk, before being evaluated via the standard of care cardiology practice. Furthermore, such detection of the change in high risk parameters is particularly informative considering that the KCCQ value increase from Week 1 to Week 2, which would otherwise suggest an improvement in the overall health risk, when in fact, the changes identified with the high risk parameters provided a different outlook.

Example 2: Exemplary Health Parameter Measurement/Data Protocols

The following are exemplary methods and cases for obtaining certain subject health parameters:

Sleeping Heart Rate & Respiratory Rate: Heart Rate (HR) and Respiratory Rate (RR) analytics during nighttime sleep. Raw HR and RR are extracted from ECG waveform every 2 minutes. HR is extracted by calculating ECG R-R interval durations, and RR is extracted by considering Heart Rate Variability (HRV) and Peak Amplitude Variation (PAV). For HR and RR at sleep, signals recorded at rest between 2 am thru 6 am (at the patient's respective time zone) may only be considered, and at least 10 minutes from any activity events within the 2 am thru 6 am interval. Summarizing this collection of 2-minute HR and RR estimates into the daily median sleeping HR and median sleeping RR is then performed. The absolute (arithmetic) and relative (multiplicative) difference between the median of the last 7 days vs. the median of the 7 days before that vs. the baseline median is calculated. The daily median sleeping HR and sleeping RR, as well as an error bar for the 5th and 95th percentile of sleeping HR and sleeping RR, for the past 7 days is plotted.

ST Segment: ST-segment elevation/depression analytics at rest and activity. The raw ECG waveform is used to detect ST segment depressions/elevations defined as a shift of the J-point by more than 0.1 mV from the isoelectric line. The daily number of beats with ST segment changes at rest vs. activity and calculate the mean daily number of beats with ST segment changes for the past 7 days is quantified. The absolute (arithmetic) and relative (multiplicative) difference between the mean of the past 7 days vs. the mean of the 7 days before that vs. the baseline mean is calculated. The daily number of beats with ST elevation/depression for the past 7 days is plotted.

Atrial fibrillation burden: Atrial Fibrillation (AF) analytics. The raw ECG waveform is used to detect the incidence and duration of AF. AF may be defined as the absence of a P wave in combination with an irregularly irregular frequency QRS complexes, often calculated as the periodicity of R waves. The daily total duration of AF and the mean of such duration for the past 7 days is calculated. The absolute (arithmetic) and relative (multiplicative) difference between the mean of the past 7 days vs. the mean of the 7 days before that vs. the baseline mean is calculated. The 2-minute HR during AF is calculated as indicated above and the greatest 2-minute HR per day is labelled as the 'Max Ventricular Response Rate'. The daily AF burden and Max Ventricular Response Rate are plotted for the past 7 days.

Activity: Patient physical activity analytics. The recorded raw accelerometer data is used to identify the presence or absence of activity as a binary indicator. A synthesis of all periods of daytime and nighttime activity into daily total hours of activity and estimate mean daily activity over the past 7 days is employed. The absolute (arithmetic) and relative (multiplicative) difference between the mean of the past 7 days vs. the mean of the 7 days before that vs. the baseline mean is calculated. The daily total number of hours of activity is plotted.

Non-Sustained Ventricular Tachycardia Runs: Non-Sustained Ventricular Tachycardia (NSVT) during AF analytics. The raw ECG waveform is used to detect ventricular tachycardia (VT) as the presence of 3 or more consecutive ventricular heartbeats at a rate of more than 100 beats per minute. In some cases, a run of less than 30 seconds is termed NSVT according to criteria of the American Heart Association (AHA). The daily number of such runs, their duration in terms of total beats, and the mean daily number of NSVT runs over the past 7 days is quantified. The absolute (arithmetic) and relative (multiplicative) difference between the mean of the past 7 days vs. the mean of the 7 days before that vs. the baseline mean is calculated. The longest NSVT run over the past 7 days by identifying the NSVT with maximum duration in terms of beats is calculated. The daily number of NSVT runs for the past 7 days is plotted.

Weight: Total body weight analytics. Total body weight readings are recorded when the patient steps on the scale (e.g., smart scale) and transmitted to the database. If more than one measurement is taken within a day, the mean for the day is used; if some of the measures taken within the day are more than 5 kg or 10% (whichever is smallest) from yesterday's reading, only the reading closest to yesterday's reading is used (as is assumed that someone else may have used the scale). The mean daily total weight over the past 7 days ('CURRENT WEIGHT'), as well as the absolute (arithmetic) and relative (multiplicative) difference the mean of the past 7 days vs. the mean of the 7 days before that vs. the baseline mean are calculated. The daily total body weight is plotted for the past 7 days.

Kansas City Cardiomyopathy Questionnaire: Answers to the 12-item Kansas City Cardiomyopathy Questionnaire (KCCQ-12). This questionnaire may only be available once a week for patients (e.g., Monday of each week). If not completed by Wednesday, the system will send an alert to the patients to ensure that it is completed (and/or the patient will be contacted by a system administrator). The multiple-choice response of each patient is recorded and displayed alongside the score allocated by the KCCQ-12. For each item, scores that are greater from the last completed questionnaire are labelled as "green," scores that remain the same are labelled as "gray," and the rest are labelled as "red." The total score and the absolute difference in the total score from the last score is displayed—the difference is colored "green" if greater, "gray" if unchanged, or "red" if lesser than the baseline KCCQ-12 (greater is better).

ECG Intervals: ECG interval duration analytics. The raw ECG waveform may be used to detect the per-beat QTc (beginning of Q wave to end of T wave, corrected), PR (beginning of P wave to start of Q wave), and QRS (beginning of Q wave to end of S wave) interval duration. Quantiles labelled as 99th ('MAX'), 50th 'MEDIAN', and 1st ('MIN') percentile are calculated over the past 7 days across all 3 metrics.

Heart Rate: 24-hour HR analytics. The raw ECG waveform is used to extract HR every 2 minutes as explained above. The 99th ('MAX'), 50th ('MEDIAN'), and 1st ('MIN') percentile HR across the past 7 days are calculated. The daily MAX, MEDIAN, and MIN HR for the past 7 days is plotted.

Blood Pressure: Seating Blood Pressure (BP) analytics. Seating blood pressure readings are recorded when the patient takes their BP and are transmitted to the system. If more than one measurement is taken within a day, the mean of the daily measures is taken. The weekly Systolic BP ('SBP') and Diastolic BP ('DBP') by taking the mean of the daily BP measurements over the past 7 days are calculated. The mean daily SBP and for the past 7 days is plotted.

Medications: Medication History. Medication names current dose, route, frequency, and the date it was prescribed, and planned stop date (if applicable) is extracted from clinical parameters provided by the subject and/or a health administrator. The medication name is matched with its record on the LOINC library, which is a widely used terminology standard for medication. Using LOINC, the system establishes whether each medication is classified as "cardiovascular" medication or not. In some cases each medication is manually correlated with a specific function (e.g., being correlated with "cardiovascular"). In some case, once manually correlated, the system is configured to automatically determine such medication in future instances of the specific function (e.g., cardiovascular). The medication name, dose, route, frequency, and the date it was prescribed is displayed. Cardiovascular medication is also displayed in the "All Patients" view of the dashboard. Medication not previously found in a patient's recorded is labelled as "started"; medication previously found but no longer available is labelled as "ended"; medication previously found at a different dose is labelled as "adjusted."

Figure 14:
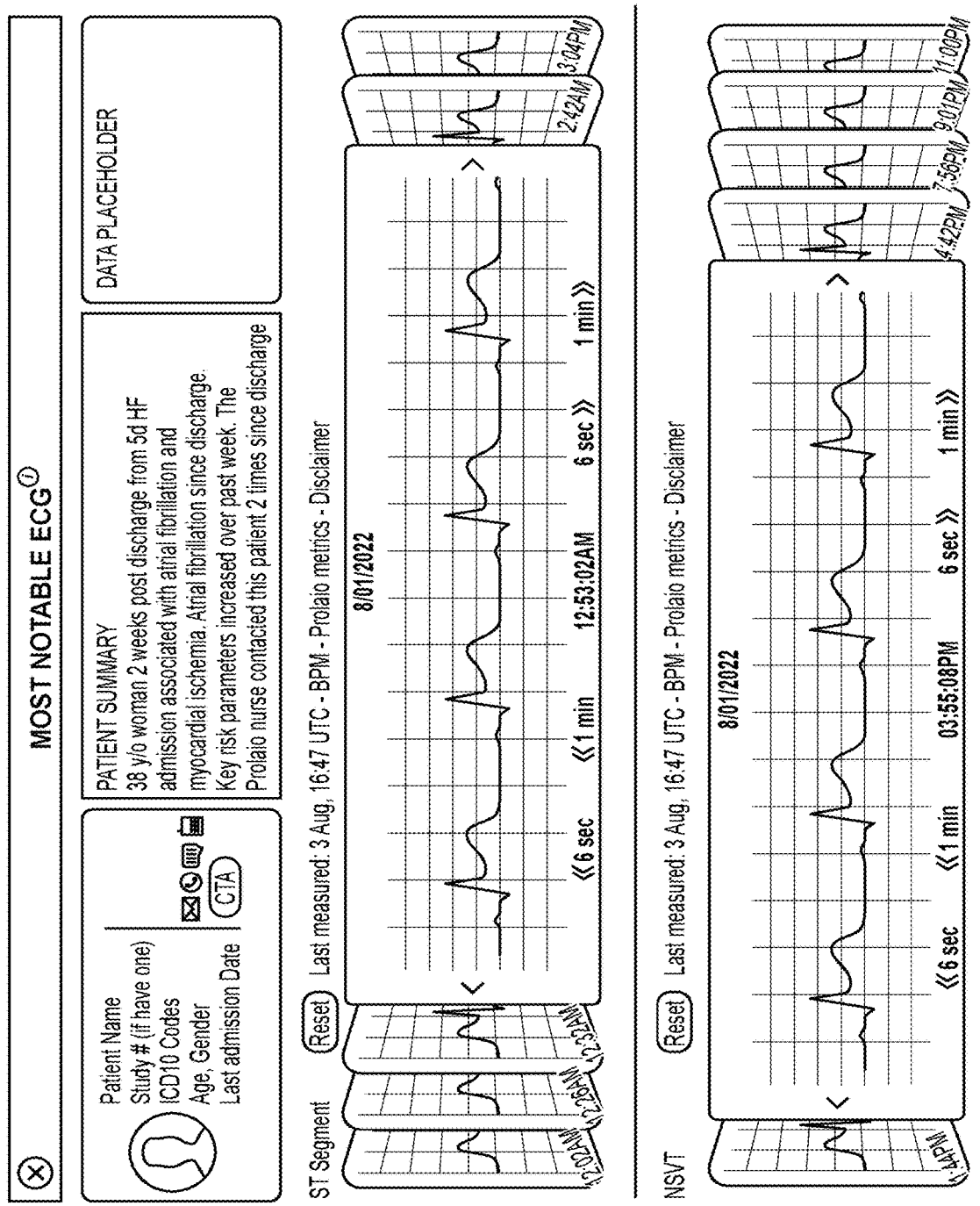
FIG. 14 depicts an exemplary output of the most notable ECGs as measured for a subject.
Figure 14:
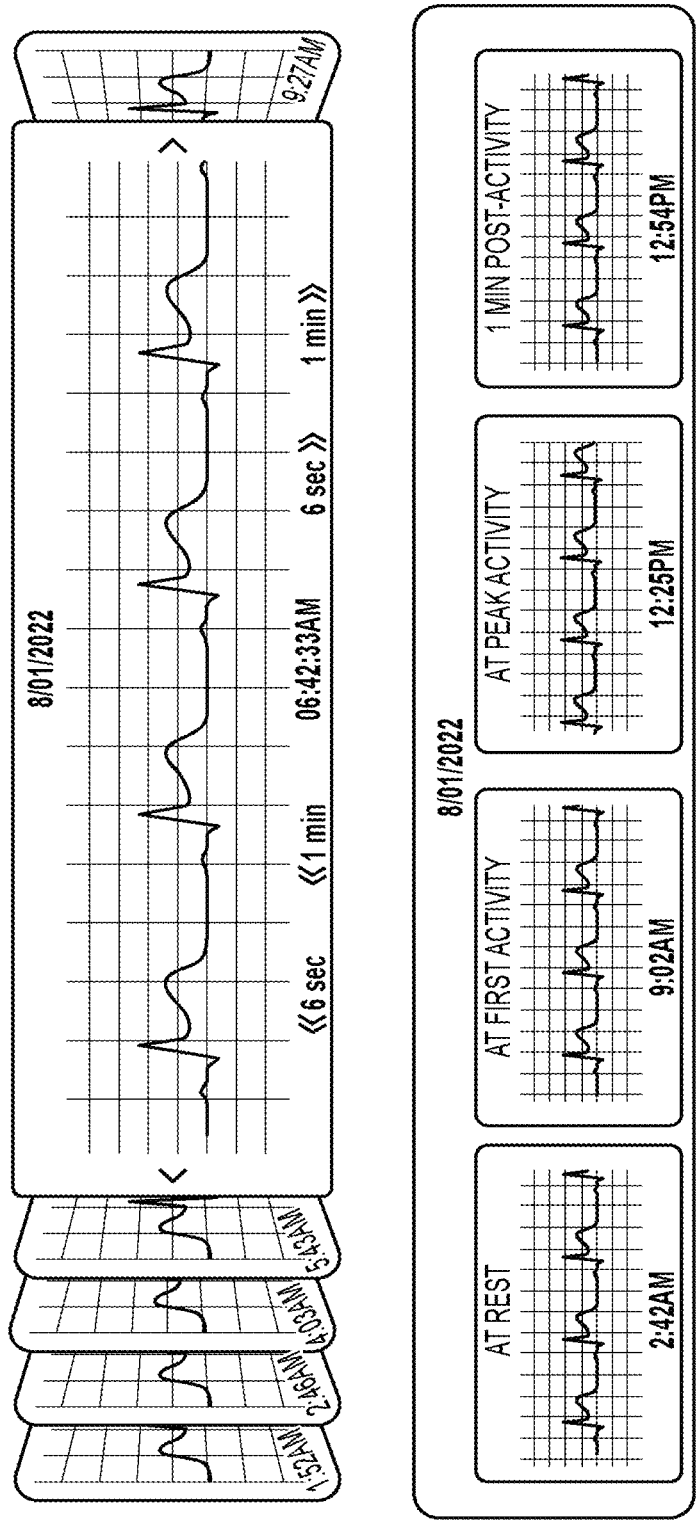
Figure 15:
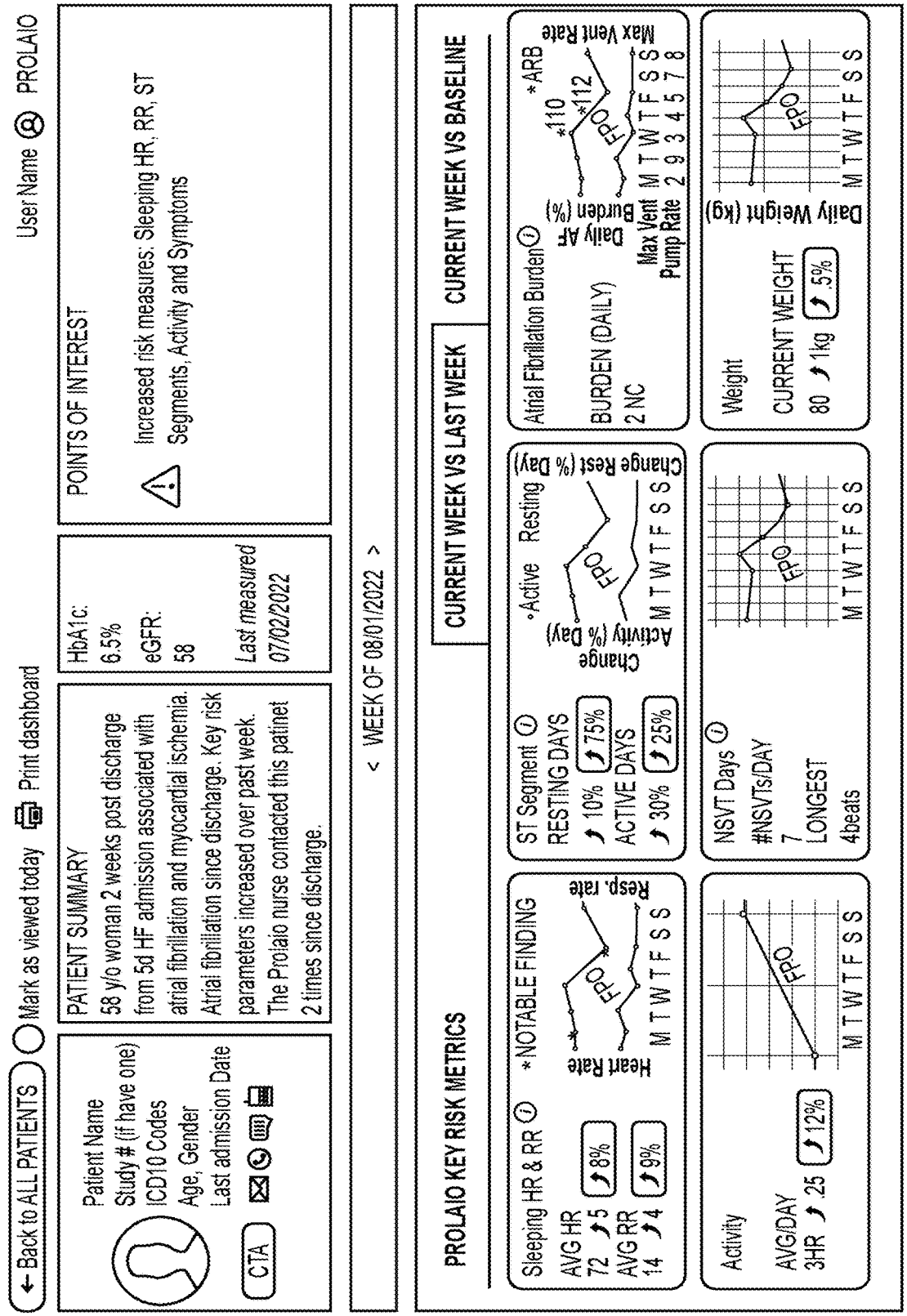
FIGS. 15-18 depicts exemplary output summaries for changes in high risk parameters and health risk status for a subject.

Most notable ECGs: A snapshot of relevant daily ECG strips. The first 1.5-second interval of ECG recordings at rest after 2 am (in the local time zone) is displayed as the 'AT REST ECG'. FIG. 14 depicts an exemplary view of the most notable ECGs display. If an abnormality is identified, these are prioritized as: ST-segment elevation/depression, NSVT, AF, or other. The longest duration of such an abnormality is identified and the first 1.5-seconds of that ECG are displayed in the defined priority. For the 'MOST NOTABLE ECG' dedicated view, all incidents of ST-segment elevation/depression, NSVT, and AF are identified and the first 3 seconds of each individual run of these abnormalities is shown. For the bottom four ECGs of the 'MOST NOTABLE ECG' view, the system provides 1.5-second strips captured as follows: 'AT REST' ECG' is captured as denoted above at 2 am (or 10 minutes after any activity occurring at 2 am); 'AT FIRST ACTIVITY' is captured at the start of any activity occurring after 6 am (local time zone) and sustained for at least 5 minutes; 'AT PEAK ACTIVITY' is captured during the highest recorded HR across all activity intervals; '1-MIN POST-ACTIVITY' is captured 1 minute after the longest period of activity in the day.

Labs-Test Results: Last recorded measures of HbA1c, eGFR and Left Ventricular Ejection Fraction (LVEF). The last recorded HbA1c, eGFR and LVEF are identified and recorded with their units and the date in which they were measured.

In some cases, changes in measurements will be calculated against the previous week and against baseline. Values occurring at and within 7 days of discharge as "baseline" values are considered. If the values of the current week are worse than those of the previous week or baseline, the absolute and relative change are displayed as red, otherwise they are displayed as green—for all measure other than 'Activity', greater is worse. If no change is detected (i.e. 0 or 0%), this is labelled as "NC" for "No Changes." Changes of more than 20% from the last 3 days may be reviewed by a system administrator as a validation check. Events of missing data for more than a day will be captured and the system may send an alert to the patients to confirm the missing data. In some cases, sleeping HR, sleeping RR, % of beats with ST-segment elevation/depression, AF burden, number of NSVT runs, total body weight, and hours of activity, mean values are calculated over the past 7 days and compared to the 7 days before that, and baseline. Changes correlated with changes including HF risk measured in clinical studies will be displayed. FIGS. 15-18 depict exemplary patient summary outputs by the system, indicating changes in high risk parameters and health risk status.

All publications, patents, patent applications and other documents cited in this application are hereby incorporated by reference herein in their entireties for all purposes to the same extent as if each individual publication, patent, patent application or other document were individually indicated to be incorporated by reference for all purposes.

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

What is claimed is:

1. A method for determining a cardiac health status for a subject, the method comprising:
   a. sensing a subject with an electrocardiogram (ECG) device to obtain ECG data, wherein the ECG device is wearable, mobile, and configured to perform ambulatory measurements of the subject;
   b. extracting one or more P wave parameters associated with the ECG data;
   c. detecting left atrial enlargement (LAE) within the subject by applying a first decision engine with the extracted one or more P wave parameters from the ECG data;
   d. determining, based on the LAE detection, a cardiac health status for the subject by applying a second decision engine, the cardiac health status comprising at least one of (i) a first cardiac condition or (ii) a first risk score for developing the first cardiac condition by the subject, wherein the first cardiac condition comprises atrial fibrillation;
   e. determining, based on the at least one of (i) the first cardiac condition or (ii) the first risk score, an adjusted cardiac health status by applying a third decision engine, the adjusted cardiac health status comprising at least one of (i) a second cardiac condition or (ii) a second risk score for developing the second cardiac condition by the subject, wherein the second cardiac condition comprises at least one of cardiomyopathy or diastolic dysfunction; and
   f. outputting onto a display interface at least one of the cardiac health status, the first cardiac condition, the first risk score, the adjusted cardiac health status, the second cardiac condition, or the second risk score.

2. The method of claim 1, wherein one or both of the first decision engine and the second decision engine comprises a trained model, a decision tree, an analytical expression, or a combination thereof.

3. The method of claim 1, wherein detecting LAE in the subject comprises applying, by the first decision engine, one or more clinical biomarker data, one or more imaging data, one or more clinical data, or a combination thereof.

4. The method of claim 1, wherein determining the cardiac health status comprises applying, by the second decision engine, one or more clinical biomarker data, one or more imaging data, one or more clinical data, the extracted one or more parameters, or a combination thereof.

5. The method of claim 1, wherein, to determine the adjusted cardiac health status, the third decision engine applies at least one of clinical biomarker data, imaging data, one or more clinical parameters for the subject, the extracted one or more parameters, or a combination thereof.

6. The method of claim 5, wherein the clinical biomarker data comprise data for one or more of B-type natriuretic peptide (BNP), N-terminal (NT)-pro hormone BNP (NT-proBNP), or cardiac troponin.

7. The method of claim 5, wherein the imaging data comprises one or both of an echocardiogram image or a cardiac MRI.

8. The method of claim 5, wherein the one or more clinical parameters comprise one or more of age, sex, weight, body mass index, height, physiological data, exercise testing results, heart rate, activity levels, velocity, sleep data, or a combination thereof.

9. The method of claim 1, wherein the ECG device comprises a 12-lead device, a 6-lead device, a 1-lead device, or a 2-lead device.

10. The method of claim 1, wherein the extracted one or more P wave parameters include at least one of P wave maximal width, variability in P wave width, P wave maximal area, variability in P wave area, or P wave slopes.

11. A system for determining a cardiac health status for a subject, the system comprising:
    an electrocardiogram (ECG) device for sensing a subject to obtain ECG data, wherein the ECG device is wearable, mobile, and configured to perform ambulatory measurements of the subject;
    one or more processors;
    one or more memories storing instructions that, when executed by the one or more processors, cause the system to perform operations including:

a. extracting one or more P wave parameters associated with the ECG data;
b. detecting left atrial enlargement (LAE) within the subject by applying a first decision engine with the extracted one or more P wave parameters from the ECG data;
c. determining, based on the LAE detection, a cardiac health status for the subject by applying a second decision engine, the cardiac health status comprising at least one of (i) a first cardiac condition or (ii) a first risk score for developing the first cardiac condition by the subject, wherein the first cardiac condition comprises atrial fibrillation; and
d. determining, based on the at least one of (i) the first cardiac condition or (ii) the first risk score, an adjusted cardiac health status by applying a third decision engine, the adjusted cardiac health status comprising at least one of (i) a second cardiac condition or (ii) a second risk score for developing the second cardiac condition by the subject, wherein the second cardiac condition comprises at least one of cardiomyopathy or diastolic dysfunction; and a display interface for outputting at least one of the cardiac health status, the first cardiac condition, the first risk score, the adjusted cardiac health status, the second cardiac condition, or the second risk score.

12. The system of claim 11, wherein, to detect LAE in the subject, the first decision engine applies at least one of clinical biomarker data, imaging data, clinical data, or a combination thereof.

13. The system of claim 11, wherein, to determine the cardiac health status, the second decision engine applies at least one of clinical biomarker data, imaging data, clinical data, the extracted one or more parameters, or a combination thereof.

14. The system of claim 11, wherein one or both of the first decision engine and the second decision engine comprises a trained model, a decision tree, an analytical expression, or a combination thereof.

15. The system of claim 11, wherein, to determine the adjusted cardiac health status, the third decision engine applies at least one of clinical biomarker data, imaging data, clinical parameters for the subject, the extracted one or more parameters, or a combination thereof.

16. The system of claim 11, wherein the ECG device comprises a 12-lead device, a 6-lead device, a 1-lead device, or a 2-lead device.

17. The system of claim 11, wherein the extracted one or more P wave parameters include at least one of P wave maximal width, variability in P wave width, P wave maximal area, variability in P wave area, or P wave slopes.

* * * * *